(12) United States Patent
Hines et al.

(10) Patent No.: US 12,723,581 B2
(45) Date of Patent: Sep. 1, 2026

(54) DIAPHRAGM PUMP DRIVE FOR AN ELECTRIC PUMP

(71) Applicant: Graco Minnesota Inc., Minneapolis, MN (US)

(72) Inventors: Bradley H. Hines, Andover, MN (US); Brian W. Koehn, Minneapolis, MN (US); Paul W. Scheierl, Chisago City, MN (US)

(73) Assignee: Graco Minnesota Inc., Minneapolis, MN (US)

( * ) Notice: Subject to any disclaimer, the term of this patent is extended or adjusted under 35 U.S.C. 154(b) by 0 days.

(21) Appl. No.: 19/203,877

(22) Filed: May 9, 2025

(65) Prior Publication Data

US 2025/0264096 A1 Aug. 21, 2025

Related U.S. Application Data

(62) Division of application No. 17/613,730, filed as application No. PCT/US2020/035844 on Jun. 3, 2020, now Pat. No. 12,392,333.

(Continued)

(51) Int. Cl.
*F04B 43/02* (2006.01)
*A61M 5/142* (2006.01)

(Continued)

(52) U.S. Cl.
CPC ....... *F04B 43/026* (2013.01); *A61M 5/14224* (2013.01); *F04B 9/02* (2013.01);

(Continued)

(58) Field of Classification Search
CPC .... F04B 43/026; F04B 43/0736; F04B 43/04; F04B 45/047; F04B 9/02; F04B 17/03;

(Continued)

(56) References Cited

U.S. PATENT DOCUMENTS 4,468,222 A * 8/1984 Lundquist ............. F04B 53/164 417/385
4,614,481 A * 9/1986 Vanderjagt ............ F04B 43/026 417/270

(Continued)

FOREIGN PATENT DOCUMENTS

CN 103977923 A 8/2014
EP 1477675 A1 † 11/2004

(Continued)

OTHER PUBLICATIONS

International Search Report and Written Opinion for PCT Application No. PCT/US2020/035844, Dated Sep. 14, 2020, pp. 15.

(Continued)

*Primary Examiner* — Peter J Bertheaud
(74) *Attorney, Agent, or Firm* — Kinney & Lange, P.A.

(57) ABSTRACT

A displacement pump includes an electrically powered drive having a drive housing. The drive is at least partially disposed in the drive housing and is configured to provide reciprocating linear motion to a diaphragm. The diaphragm is captured between an adaptor mountable to the drive housing and a fluid cover. The adaptor includes an inner mounting portion interfacing with the drive housing and an outer mounting portion interfacing with the diaphragm. Multiple adaptors having multiple outer mounting portion diameters can be mounted to the same drive housing. Each of the multiple adaptors have the same inner mounting portion configuration to mount to the same drive housing. The adaptors can mount to the drive housing in multiple orientations while the fluid cover can mount to the adaptor in a single orientation.

20 Claims, 27 Drawing Sheets

Related U.S. Application Data

(60) Provisional application No. 62/856,354, filed on Jun. 3, 2019.

(51) Int. Cl.

| | |
|---|---|
| ***F04B 9/02*** | (2006.01) |
| ***F04B 17/03*** | (2006.01) |
| ***F04B 35/04*** | (2006.01) |
| ***F04B 43/00*** | (2006.01) |
| ***F04B 43/04*** | (2006.01) |
| ***F04B 43/06*** | (2006.01) |
| ***F04B 43/073*** | (2006.01) |
| ***F04B 45/04*** | (2006.01) |
| ***F04B 45/047*** | (2006.01) |
| ***F04B 53/16*** | (2006.01) |
| ***F04B 53/22*** | (2006.01) |

(52) U.S. Cl.

CPC .............. *F04B 17/03* (2013.01); *F04B 35/04* (2013.01); *F04B 43/0054* (2013.01); *F04B 43/025* (2013.01); *F04B 43/04* (2013.01); *F04B 43/06* (2013.01); *F04B 43/0736* (2013.01); *F04B 45/043* (2013.01); *F04B 45/047* (2013.01); *F04B 53/16* (2013.01); *F04B 53/22* (2013.01); *A61M 2205/12* (2013.01)

(58) Field of Classification Search

CPC ........ F04B 35/04; F04B 43/02; F04B 43/025; F04B 43/06; F04B 43/0054; F04B 45/043; F04B 53/22; F04B 53/16; A61M 5/14224; A61M 2205/12

See application file for complete search history.

(56) References Cited

U.S. PATENT DOCUMENTS

| | | | | |
|---|---|---|---|---|
| 4,856,966 | A | 8/1989 | Ozawa | |
| 5,282,724 | A | 2/1994 | Reynolds | |
| 5,730,587 | A | 3/1998 | Snyder et al. | |
| 5,749,709 | A | 5/1998 | Du | |
| 5,860,793 | A | 1/1999 | Muscarella et al. | |
| 6,318,967 | B1 | 11/2001 | Wirz et al. | |
| 7,063,517 | B2 * | 6/2006 | Towne ................ | F04B 43/0736 137/625.66 |
| 7,318,422 | B2 | 1/2008 | Douyama et al. | |
| 7,661,933 | B2 | 2/2010 | Ohya | |
| 8,328,537 | B2 * | 12/2012 | Rochat ................ | A61M 5/1413 604/153 |
| 9,028,224 | B2 * | 5/2015 | Headley .............. | F04B 43/0736 137/625.25 |
| 9,638,185 | B2 * | 5/2017 | Hines .................... | F04B 43/025 |
| 10,156,232 | B2 * | 12/2018 | Duquette ............ | A61M 16/208 |
| 2010/0045096 | A1 | 2/2010 | Schonlau et al. | |
| 2012/0107152 | A1 | 5/2012 | Maguire et al. | |
| 2013/0101438 | A1 | 4/2013 | Cedrone et al. | |
| 2014/0023532 | A1 | 1/2014 | Ishii et al. | |
| 2015/0147202 | A1 | 5/2015 | Weiss | |
| 2015/0226192 | A1 | 8/2015 | Hines et al. | |
| 2017/0298920 | A1 | 10/2017 | Verdugo et al. | |
| 2018/0291882 | A1 * | 10/2018 | Algawi ............... | A61M 3/0254 |
| 2019/0048871 | A1 | 2/2019 | Hayes-Pankhurst et al. | |

FOREIGN PATENT DOCUMENTS

| | | | |
|---|---|---|---|
| EP | 2634429 | A1 | 9/2013 |
| GB | 2550484 | A | 11/2017 |
| JP | 2004138009 | A | 5/2004 |
| WO | 0127475 | A1 | 4/2001 |
| WO | WO2017193037 | A1 † | 11/2017 |

OTHER PUBLICATIONS

First Chinese Office Action for CN Application No. 202080041136.0, Dated Dec. 2, 2022, pp. 22.

Second Chinese Office Action for CN Application No. 202080041136.0, Dated Jun. 6, 2023, pp. 6.

* cited by examiner

† cited by third party

P
50b
22a
34a
36a
50a
42a
44
38a
46a
40
28
24
26
48
32
18
20
30
16
14

38
42
58
40

38
114
112
118
126
116
40
128
122
120
42
44
124
124

38
44
114
120
120
126
118
116
40
112
128
42
124
124

34
38
134
132a
134

136
34
132
10
B
134

DIAPHRAGM PUMP DRIVE FOR AN ELECTRIC PUMP

CROSS-REFERENCE TO RELATED APPLICATIONS

This application is a divisional application of U.S. patent application Ser. No. 17/613,730 filed Nov. 23, 2021, and entitled "DIAPHRAGM PUMP DRIVE FOR AN ELECTRIC PUMP," which is a national stage application of International Patent Application No. PCT/US2020/035844 filed Jun. 3, 2020, and entitled "DIAPHRAGM PUMP DRIVE FOR AN ELECTRIC PUMP," which claims the benefit of U.S. Provisional Application No. 62/856,354 filed Jun. 3, 2019, and entitled "DIAPHRAGM PUMP DRIVE," the disclosures of which are hereby incorporated by reference in their entireties.

BACKGROUND

This disclosure relates generally to pumps. More particularly, this disclosure relates to pump drive systems.

Positive displacement pumps discharge a process fluid at a selected flow rate. In a typical positive displacement pump, a fluid displacement member, usually a piston or diaphragm, drives the process fluid through the pump. When the fluid displacement member is drawn in, a suction condition is created in the fluid flow path, which draws process fluid into a fluid cavity from the inlet manifold. The fluid displacement member then reverses direction and forces the process fluid out of the fluid cavity through the outlet manifold.

Displacement pumps include a drive system that powers the displacement member through the respective pumping and suction strokes. The drive system can be, pneumatic, hydraulic, or mechanical. For example, a pneumatic or hydraulic drive can route fluid to alternating chambers to cause reciprocation of the drive member. A mechanical drive converts a rotary output to a linear input to drive reciprocation. The mechanical drive can be powered electrically, pneumatically, or hydraulically and represents a relatively expensive component of the pump.

SUMMARY

According to one aspect of the disclosure, a displacement pump includes an electric drive having a drive housing defining a pump axis and a first fluid module mountable to an end of the drive housing. The first fluid module includes a first adaptor configured to interface with the drive housing, the first adaptor comprising a first inner mounting portion and a first outer mounting portion, wherein the first inner mounting portion interfaces with the drive housing at a first interface; a first cover configured to interface with the first outer mounting portion at a second interface; and a first diaphragm captured between the first adaptor and the first cover. A drive component of the electric drive disposed within the drive housing is accessible from outside of the drive housing through a central aperture of the first adaptor with the first adaptor interfacing with the drive housing.

According to an additional or alternative aspect of the disclosure, a displacement pump assembly includes an electric drive having a drive housing defining a pump axis; a first fluid module mountable to an end of the drive housing; and a second fluid module mountable to the end of the drive housing. The first fluid module includes a first adaptor configured to interface with the drive housing, the first adaptor comprising a first inner mounting portion and a first outer mounting portion, the first inner mounting portion configured to interface with the drive housing at a first interface; a first cover configured to interface with the first outer mounting portion at a second interface; and a first diaphragm captured between the first adaptor and the first cover. The second fluid module includes a the second fluid module including a second adaptor configured to interface with the drive housing at the first interface, a second cover that mounts to the second adaptor, and a second diaphragm captured between the second adaptor and the second cover. The second adaptor includes a second inner mounting portion and a second outer mounting portion, the second inner mounting portion configured to interface with the drive housing at the first interface. A first diameter of the first diaphragm is different than a second diameter of the second diaphragm.

According to another additional or alternative aspect of the disclosure, a method of servicing an electrically-powered displacement pump includes removing a first fluid cover from a first adaptor; and accessing, through the first adaptor, drive components disposed in a drive housing on which the first adaptor is mounted and within which at least one component configured to rotate about a motor axis is disposed.

According to yet another additional or alternative aspect of the disclosure, a displacement pump includes an electric drive having a drive housing defining a pump axis and a first fluid module mountable to an end of the drive housing. The first fluid module includes a first adaptor configured to interface with the drive housing, the first adaptor comprising a first inner mounting portion and a first outer mounting portion, a first cover configured to interface with the first outer mounting portion at a second interface, and a first diaphragm captured between the first adaptor and the first cover. The first inner mounting portion interfaces with the drive housing at a first interface. The first interface allows the first adaptor to be mounted at a plurality of adaptor mount positions. The second interface is a clocked interface that allows the first cover to be mounted at a single cover mount position.

DETAILED DESCRIPTION

Figure 1A:
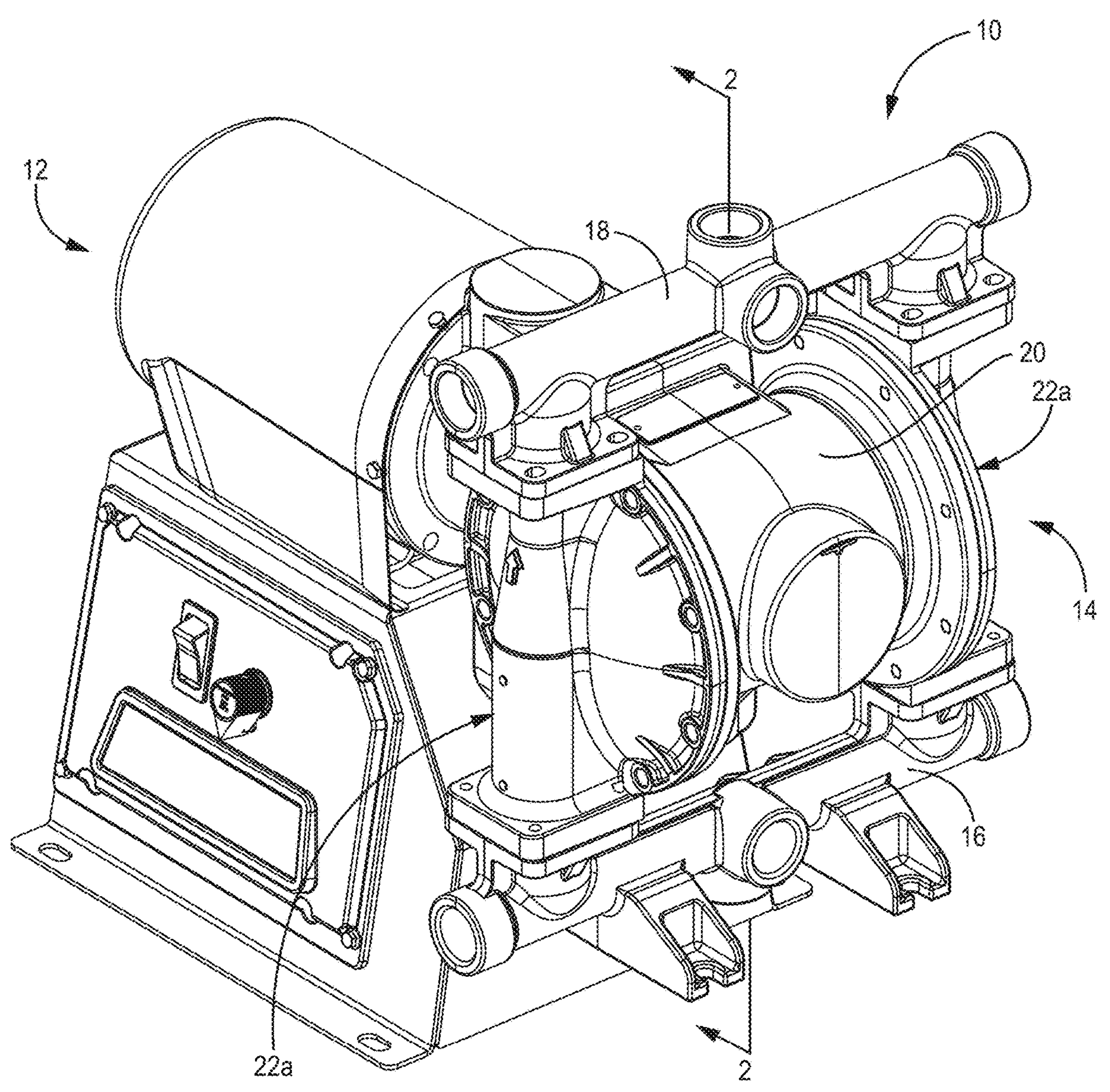
FIG. 1A is an isometric view of an electrically operated pumping assembly.
Figure 1B:
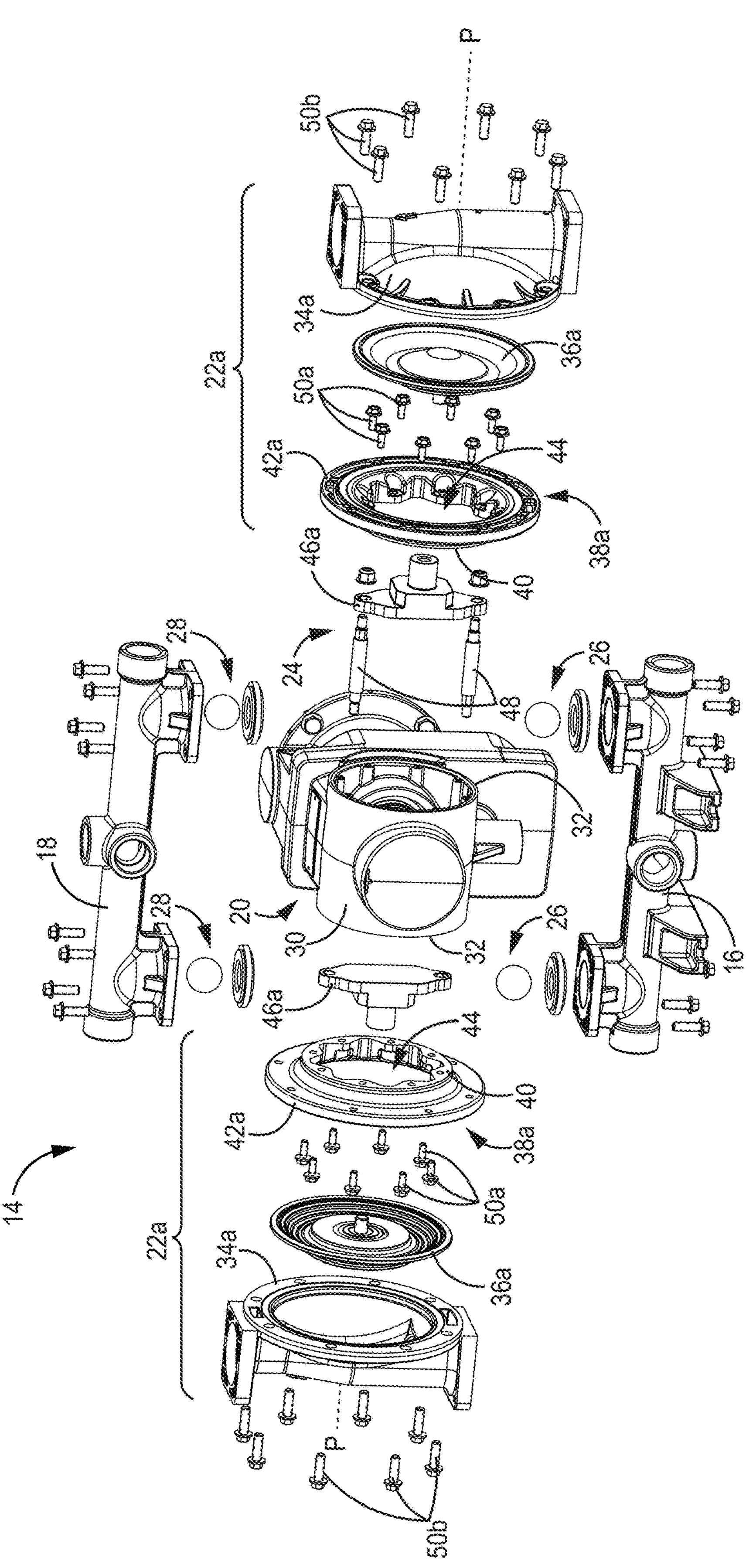
FIG. 1B is an exploded view of the electrically operated pumping assembly shown in FIG. 1A.

FIG. 1A is an isometric view of pumping assembly 10, which includes motor 12 and pump 14. FIG. 1B is an exploded view of pump 14. FIGS. 1A and 1B will be discussed together. Pump 14 includes inlet manifold 16, outlet manifold 18, drive housing 20, fluid modules 22*a*, drive 24, inlet check valves 26, and outlet check valves 28. Drive housing 20 includes body 30 having ends 32. Each fluid module 22*a* includes fluid cover 34*a*, diaphragm 36*a*, and adaptor 38*a*. Each adaptor 38*a* includes inner mounting portion 40, outer mounting portion 42*a*, and central aperture 44. Drive 24 includes bearing plates 46*a* and rods 48.

Pumping assembly 10 is configured to pump fluid from an upstream location to a downstream location. The fluid can be a liquid or a gas. Pump 14 pumps the fluid and motor 12 powers pump 14. Motor 12 can be an electric motor configured to receive electrical energy, such as through a standard electrical outlet, and converts electrical energy to rotational output motion. For example, motor 12 can be a brushed or brushless DC motor, among other options. In some examples, a gearbox is disposed between motor 12 and drive 24. The rotational output of motor 12 is converted into linear reciprocating motion by drive 24 to displace diaphragms 36*a* through respective pumping and suction strokes.

Pump 14 is connected to motor 12 and configured to be powered by motor 12. Pump 14 includes inlet manifold 16 through which fluid is introduced to pump 14. Pump 14 further includes outlet manifold 18 through which pumped fluid is output from pump 14. Drive housing 20 is disposed between inlet manifold 16 and outlet manifold 18. Drive housing 20 contains at least a portion of drive 24. Drive housing 20 can be formed by one or more components. Drive housing 20 facilitates mounting of fluid modules 22. Drive 24 is at least partially disposed within body 30 and is configured to covert the rotational output of motor 12 to a reciprocating linear input to power pump 14. Drive 24 can be fully or partially contained within drive housing 20.

Fluid modules 22*a* are mounted to ends 32 of drive housing 20. Drive housing 20 is thereby disposed axially between fluid modules 22*a*. Pump 14 is shown as including dual fluid modules 22. It is understood, however, that pump 14 can include a single fluid module 22 in some examples. Fluid modules 22*a* are disposed coaxially on pump axis P-P.

For each fluid module 22*a*, adaptor 38*a* is configured to mount to an end 32 of drive housing 20. In some examples, adaptor 38*a* is in direct contact with drive housing 20. Inner mounting portion 40 interfaces with drive housing 20. Fasteners 50*a*, such as bolts, extend through inner mounting portion 40 and into drive housing 20 to secure adaptor 38*a* to drive housing 20. As such, adaptor 38*a* mounts fluid module 22*a* to drive housing 20. Fluid cover 34*a* is configured to mount to adaptor 38*a*. Fluid covers 34*a* define the axial ends of pump 14. In some examples, fluid cover 34*a* is in direct contact with adaptor 38*a*. Outer mounting portion 42*a* interfaces with fluid cover 34*a*. Fasteners 50*b*, such as bolts, extend through fluid cover 34*a* and into adaptor 38*a* to secure fluid cover 34*a* to adaptor 38*a*. Diaphragm 36*a* is retained between adaptor 38*a* and fluid cover 34*a*. More specifically, diaphragm 36*a* is retained between and forms a seal between outer mounting portion 42*a* and fluid cover 34*a*. A pumping chamber 56 (FIG. 2) is defined between diaphragm 36*a* and fluid cover 34*a*. The center of the diaphragm 36*a* is moved during a pump cycle while the peripheral edge of the diaphragm 36*a* is held in place between fluid cover 34*a* and adaptor 38*a* to increase and decrease the volume of the pumping chamber 56 to pump fluid. In the example shown, pump assembly 10 can be considered to be an electrically operated double diaphragm (EODD) pump.

Adaptors 38*a* extend between inner mounting portion 40 and outer mounting portion 42*a*. Inner mounting portion 40 has a first diameter and outer mounting portion 42*a* has a second diameter. The second diameter is larger than the first diameter such that adaptor 38*a* expands the diameter of fluid module 22*a* relative drive housing 20. As such, the diameter of fluid module 22*a* expands from a smaller diameter facing drive housing 20 to a larger diameter facing away from drive housing 20.

Inlet check valves 26 are disposed between inlet manifold 16 and fluid covers 34*a*. Outlet check valves 28 are disposed between outlet manifold 18 and fluid covers 34*a*. The flow of fluid being pumped is regulated by inlet check valves 26 and outlet check valves 28. Inlet check valves 26 regulate flow into pumping chambers 56 and outlet check valves 28 regulate flow out of pumping chambers 56.

Bearing plates 46*a* are disposed within drive housing 20. Rods 48 extend between and connect the bearing plates 46*a*. Each bearing plate 46*a* is connected to a diaphragm 36*a* through central aperture 44 of adaptor 38*a*. In the example shown, bearing plates 46*a* are configured to provide the linear input to diaphragms 36*a* to drive reciprocation of diaphragms 36*a*. Rods 48 link bearing plates 46*a* together such that bearing plates 46*a* are linked for simultaneous reciprocation.

Figure 2:
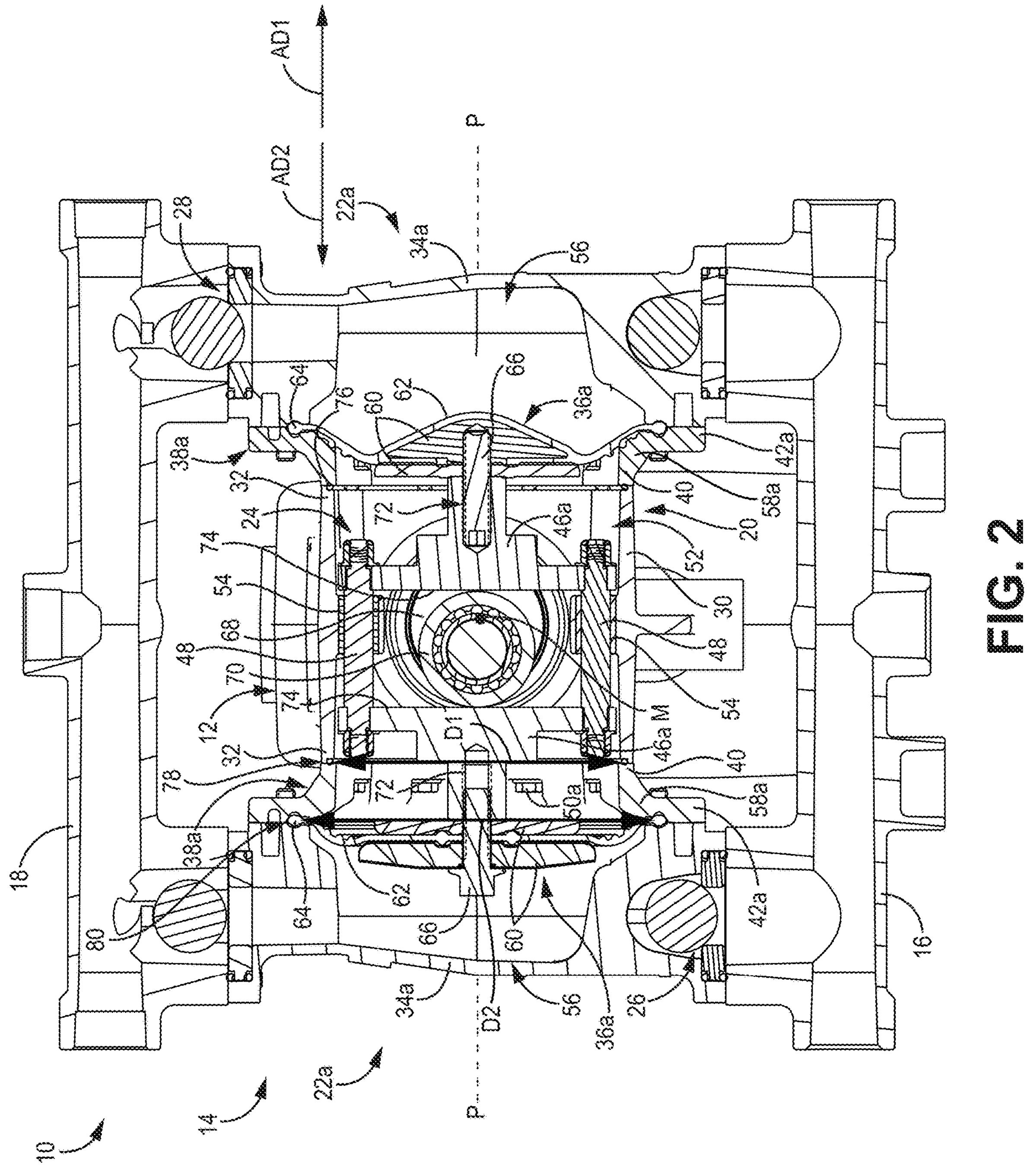
FIG. 2 is a cross-sectional view taken along line 2-2 in FIG. 1A.

FIG. 2 is a cross-sectional view of pumping assembly 10 taken along line 2-2 in FIG. 1A. Pumping assembly 10 includes motor 12 and pump 14. Pump 14 includes inlet manifold 16, outlet manifold 18, drive housing 20, fluid modules 22*a*, drive 24, inlet check valves 26, and outlet check valves 28. Drive housing 20 includes body 30 and ends 32 and at least partially defines drive chamber 52. Drive housing 20 further includes rod sleeves 54. Each fluid module 22*a* includes fluid cover 34*a*, diaphragm 36*a*, adaptor 38*a*, and pumping chamber 56. Each adaptor 38*a* includes inner mounting portion 40, outer mounting portion 42*a*, and transition portion 58*a*. Diaphragms 36*a* include diaphragm plates 60, membranes 62, circumferential edge 64, and connectors 66. Drive 24*a* includes bearing plates 46*a*, rods 48, eccentric 68, and bearing 70. Bearing plates 46*a* including mounting bores 72 and bearing surface 74.

Motor 12 is connected to drive housing 20. Drive 24 is at least partially disposed within drive chamber 52. Motor 12 is configured to generate a rotational output and drive 24 is configured to convert that rotational output into a linear input to drive displacement of diaphragms 36*a* along pump axis P-P and cause pumping by pump 14.

Bearing 70 is connected to eccentric 68 to be moved in a circular path offset from a central axis of rotation M of eccentric 68. Bearing 70 is disposed between and interfaces with bearing plates 46*a*, which are also disposed in drive chamber 52. More specifically, bearing 70 interfaces with bearing surface 74 of each bearing plate 46*a*. Rods 48 extend between and fix bearing plates 46*a* relative each other such that bearing plates 46*a* move simultaneously. In some examples, rods 48 have threaded ends that are connected to nuts on the outer axial sides of bearing plates 46*a*. Rods 48 extend through rod sleeves 54 formed in drive chamber 52. In the example shown, rod sleeves 54 are formed by drive housing 20. Rods 48 reciprocate within rod sleeves 54. Rod sleeves 54 fix rods 48 to reciprocate axially along pump axis P-P. The bearing plates 46*a* and rods 48 form a carriage that moves linearly along pump axis P-P to move, via connectors 66, the centers of the diaphragms 36*a* as driven by the eccentric 68 and bearing 70. Bearing plates 46*a* are pushed by the bearing 70 axially, left and right. Bearing 70 does not push on anything as it moves vertically, thus the eccentric 68, bearing 70, and bearing plates 46*a* convert rotational motion into axial reciprocating motion which drives the diaphragms 36*a.*

Fluid modules 22*a* are mounted to opposite axial ends 32 of drive housing 20. A first one of fluid modules 22*a* is mounted to a first end 32 and a second one of fluid modules 22*a* is mounted to a second end 32. Adaptors 38*a* are mounted to drive housing 20 and support the other components of fluid modules 22*a*. Inner mounting portion 40 is connected to drive housing 20 to secure fluid modules 22*a* to drive housing 20. Fasteners 50*a* extend through inner mounting portion 40 into drive housing 20 to secure adaptors 38*a* to drive housing 20. In the example shown, at least a portion of the fastener 50*a* is exposed within drive chamber 52.

Inner mounting portion 40 interfaces with drive housing 20 at first interface 78. Inner mounting portion 40 contacts drive housing 20 at first interface 78. Inner mounting portion 40 seals with the end 32 of drive housing 20 with adaptor 38*a* mounted to drive housing 20. In the example shown, annular seal 76 is disposed between drive housing 20 and inner mounting portion 40. Annular seal 76 can be an o-ring, among other options. Annular seal 76 can be disposed in a notch formed in end 32 of drive housing 20. It is understood that inner mounting portion 40 can include a groove or notch configured to receive annular seal 76. The groove or notch in inner mounting portion 40 can be in addition to or replacement of the notch formed in drive housing 20.

Fluid covers 34*a* are disposed between and fluidly connected to inlet manifold 16 and outlet manifold 18. Fluid covers 34*a* are connected to outer mounting portions 42*a* of adaptors 38*a*. Fluid covers 34*a* contact outer mounting portion 42*a* at second interface 80. Diaphragms 36*a* are captured between fluid covers 34*a* and adaptors 38*a*. M ore specifically, circumferential edge 64 is captured between adaptor 38*a* and fluid cover 34*a*. Circumferential edge 64 can include a bead disposed within grooves formed in outer mounting portion 42*a* and fluid cover 34*a*. Circumferential edge 64 forms an annular seal between fluid covers 34*a* and outer mounting portion 42*a*. In the example shown, complimentary grooves are formed on each of outer mounting portion 42*a* and fluid cover 34*a* to receive circumferential edge 64. Diaphragms 36*a* seal between drive chamber 52 and pumping chamber 56. The inner side of each diaphragm 36*a* is exposed to drive chamber 52 such that any fluid (e.g., air, hydraulic fluid, etc.) within drive chamber 52 can be in contact with either one of diaphragms 36*a.*

Inner mounting portions 40 have a first diameter D1 at first interface 78. Outer mounting portions 42*a* have a second diameter D2 at second interface 80. The second diameter D2 is larger than the first diameter D1 such that adaptor 38*a* expands in diameter relative drive housing 20. Transition portion 58*a* extends between and connects inner mounting portion 40 and outer mounting portion 42*a*. Transition portion 58*a* increases the diameter of adaptor 38*a* between inner mounting portion 40 and outer mounting portion 42*a*. The larger diameter of outer mounting portion 42*a* facilitates a larger diaphragm 36*a*. Diaphragm 36*a* has a diameter larger than a diameter of drive housing 20.

Membrane 62 of diaphragm 36*a* is a flexible membrane. Diaphragm plates 60 interface with membrane 62. Connectors 66 extend through an inner one of diaphragm plates 60 and extend at least partially through an outer one of diaphragm plates 60.

Connectors 66 are disposed on axis P-P and are connected to bearing plates 46*a*. Connectors 66 extend into mounting bores 72 formed in bearing plates 46*a*. Connectors 66 fix bearing plates 46*a* to the centers of diaphragms 36*a*. Bearing plates 46*a* can thereby drive diaphragms 36*a* through each of the pressure stroke, during which the volume of pumping chamber 56 is reduced and fluid is driven through outlet check valve 28 from pumping chamber 56 to outlet manifold 18, and the suction stroke, during which the volume of pumping chamber 56 is expanded and fluid is drawn through inlet check valve 26 to pumping chamber 56 from inlet manifold 16.

Drive chamber 52 is defined axially between an inner (facing towards drive housing 20) side of each diaphragm 36*a*. Pumping chambers 56 are defined between the outer (facing away from drive housing 20) side of each diaphragm 36*a* and fluid covers 34*a*.

During operation, motor 12 receives electric power and generates a rotational output. Drive 24 converts the rotational output of motor 12 to linear movement of diaphragms 36*a*. Drive 24 moves the centers of the diaphragms 36*a* back and forth in axial directions AD1 and AD2, increasing and decreasing the volumes of pumping chambers 56. Inlet check valves 26 and outlet check valves 28 regulate the flow of fluid through the pumping chambers 56 from an upstream to downstream direction.

The rotational output drives rotation of eccentric 68 about axis M. Bearing 70 rotates in a circular path about axis M. Bearing 70 interfaces with bearing surfaces 74 of bearing plates 46*a* and exerts a driving force on bearing plates 46*a*. Rods 48 link bearing plates 46*a* for simultaneous movement. For example, bearing 70 can move in a clockwise path from the position shown in FIG. 2. Bearing 70 exerts a driving force on the bearing plate 46*a* disposed on the right-hand side of bearing 70 (in the view of FIG. 2) and pushes that bearing plate 46*a* in axial direction AD1 to drive the diaphragm 36*a* associated with that bearing plate 46*a* through a pumping stroke. Rods 48 pull the other bearing plate 46*a* in axial direction AD1 to pull the diaphragm 36*a* associated with that bearing plate 46*a* through a suction stroke. Diaphragms 36*a* are reciprocated on pump axis P-P through alternating pumping and suction strokes to pump the fluid.

Figure 3A:
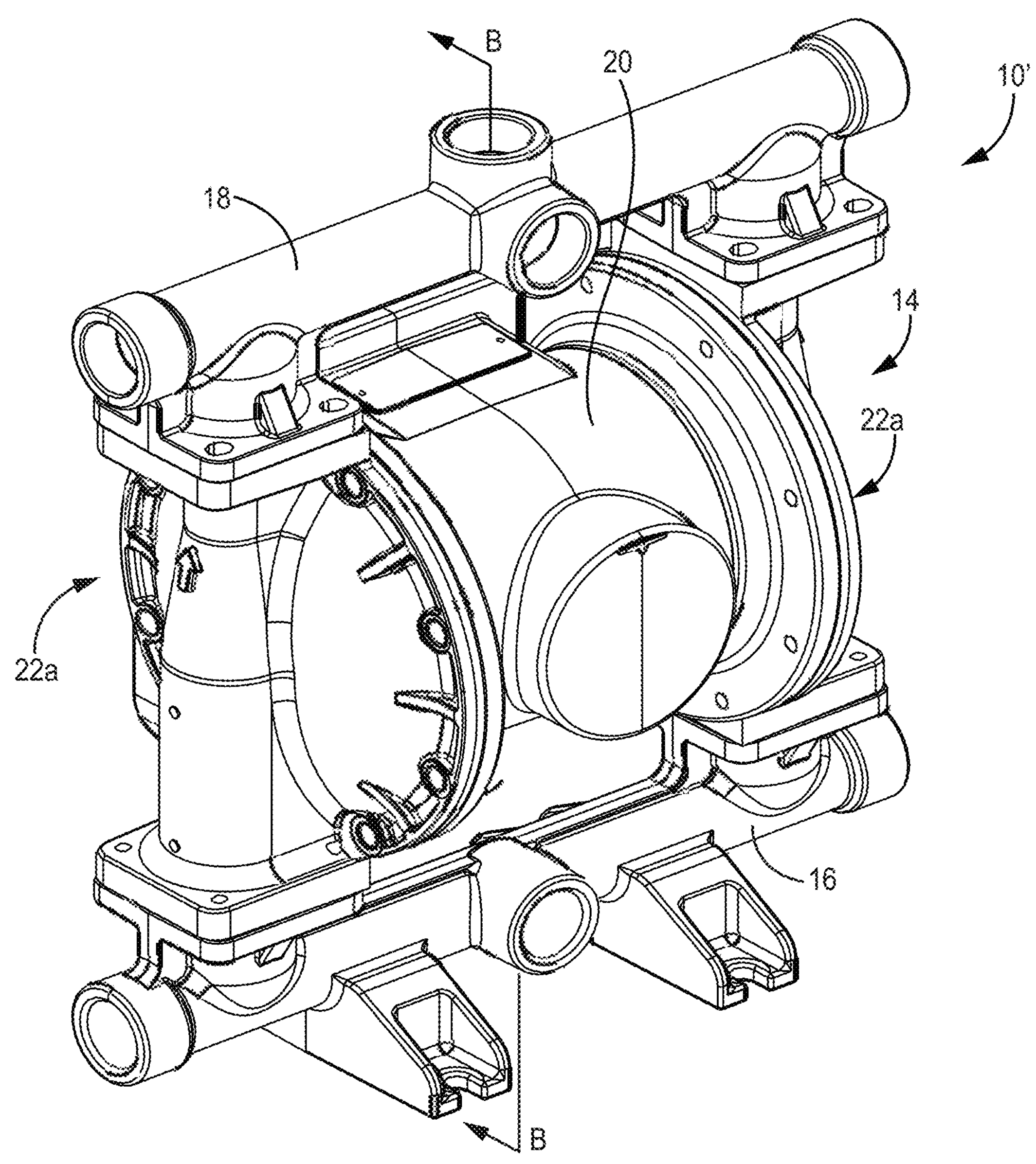
FIG. 3A is an isometric view of a second electrically operated pumping assembly.
Figure 3B:
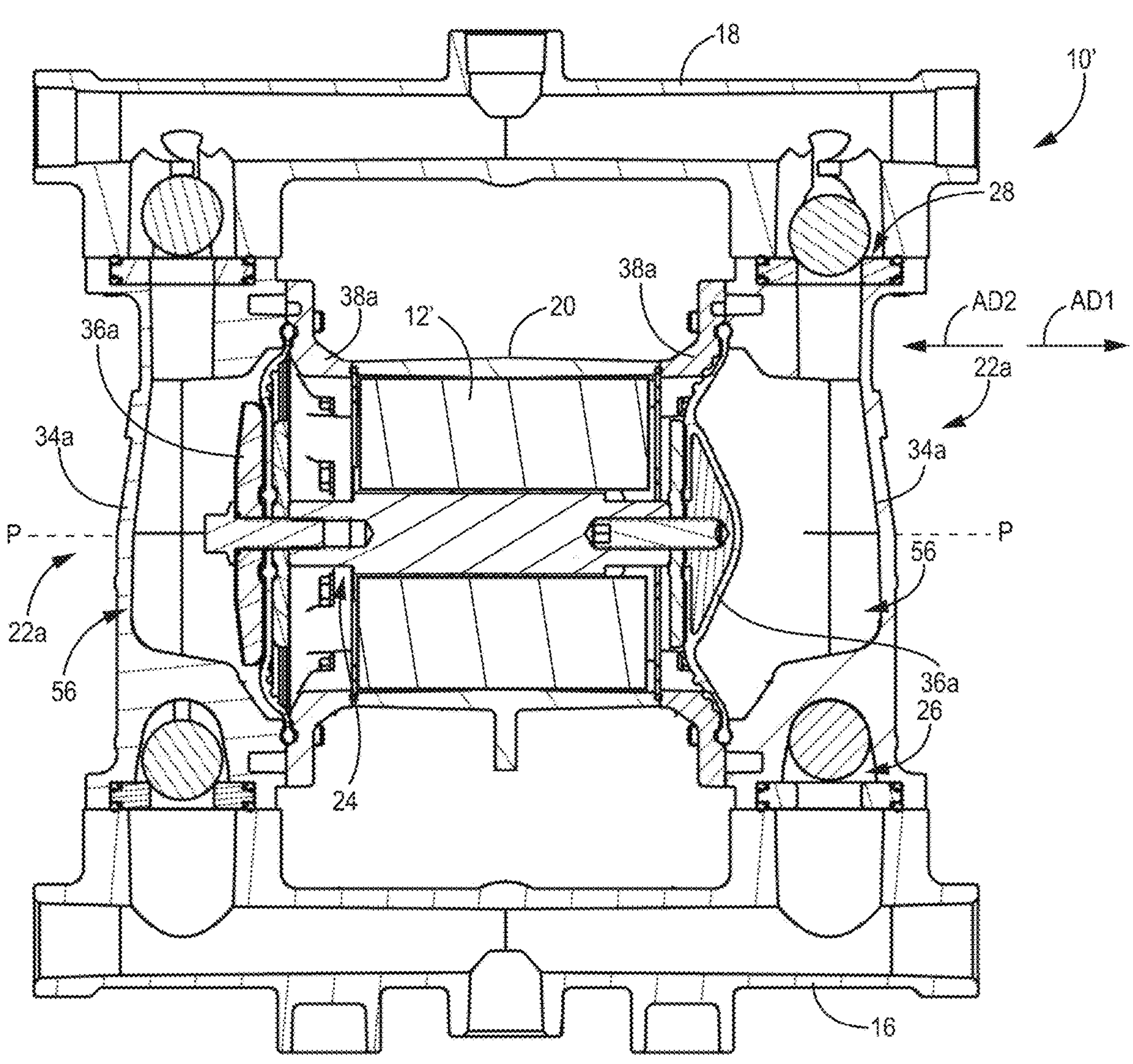
FIG. 3B is a cross-sectional view taken along line B-B in FIG. 3A.

FIG. 3A is an isometric view of pumping system 10', which includes motor 12' and pump 14. FIG. 3B is a cross-sectional view taken along line B-B in FIG. 3A. Pumping system 10' is substantially similar to pumping system 10 (FIGS. 1A-2) except motor 12' of pumping system 10' is disposed within drive housing 20.

Motor 12' is disposed within drive housing 20 and is coaxial with pump axis P-P. Motor 12' is disposed axially between fluid modules 22*a*. Motor 12' is electrically powered and configured to drive diaphragms 36*a* in at least one of first axial direction AD1 and second axial direction AD2. Drive 24 is disposed coaxially with motor 12' on pump axis P-P. Drive 24 is connected to diaphragms 36*a* to drive diaphragms 36*a* linearly along pump axis P-P.

In some examples, motor 12' is configured to generate a rotational output and drive 24 is configured to convert the rotational output to a linear input to displace diaphragms 36. For example, motor 12' can be a rotor/stator motor and drive 24 can receive the rotational output from the rotor, convert that rotational output to a linear input, and provide the linear input to diaphragms 36. For example, drive 24 can include a ball screw or roller screw. The screw can be connected to the diaphragms 36 to displace diaphragms. The motor 12' can be a reversible motor that rotates in a first rotational direction about pump axis P-P to cause diaphragms 36 to displace in one of first axial direction AD1 and second axial direction AD2 and rotates in a second, opposite rotational direction to cause diaphragms to displace in the other one of first axial direction AD1 and second axial direction AD2.

In some examples, motor 12' can be a solenoid configured to linearly displace drive 24. For example, motor 12' can be a double-acting solenoid configured to magnetically displace drive 24 in each of first axial direction AD1 and second axial direction AD2. Drive 24 can be an armature including a permanent magnet. In other examples, motor 12' can be a single-acting solenoid configured to magnetically displace drive 24 in one of first axial direction AD1 and second axial direction AD2, while drive 24 is mechanically displaced in the other one of first axial direction AD1 and second axial direction AD2. For example, a spring can displace drive 24 in the other one of the first axial direction AD1 and the second axial direction AD2.

Fluid modules 22 can be utilized across a variety of pumps 14 having the same drive housing 20 but different motor configurations. Fluid modules 22 can thereby be changed between pumps 14 having different drive and motor configurations and/or components and can provide access to those configurations and components without requiring dismounting of adaptors 38.

FIGS. 4A-4H illustrate a sequence of removing fluid modules 22*a* from drive housing 20 and installing second fluid modules 22*b* on drive housing 20. The removal of one of fluid modules 22*a* and replacement with one of second fluid modules 22*b* is discussed in detail. It is understood that the process is the same for removing the other one of fluid modules 22*a* and installing the other one of second fluid modules 22*b*. Fluid modules 22*a*, 22*b* can be referred to collectively herein as "fluid modules 22." Both fluid modules 22 would typically be removed and replaced at the same time, in the same way. FIGS. 4A-4D show the process of removing fluid module 22*a*. It is understood that fluid module 22*a* can be installed in the reverse order of removal. FIGS. 4E-4H show the process of installing fluid module 22*b* on drive housing 20. It is understood that fluid module 22*b* can be removed in the reverse order of installation.

Figure 4A:
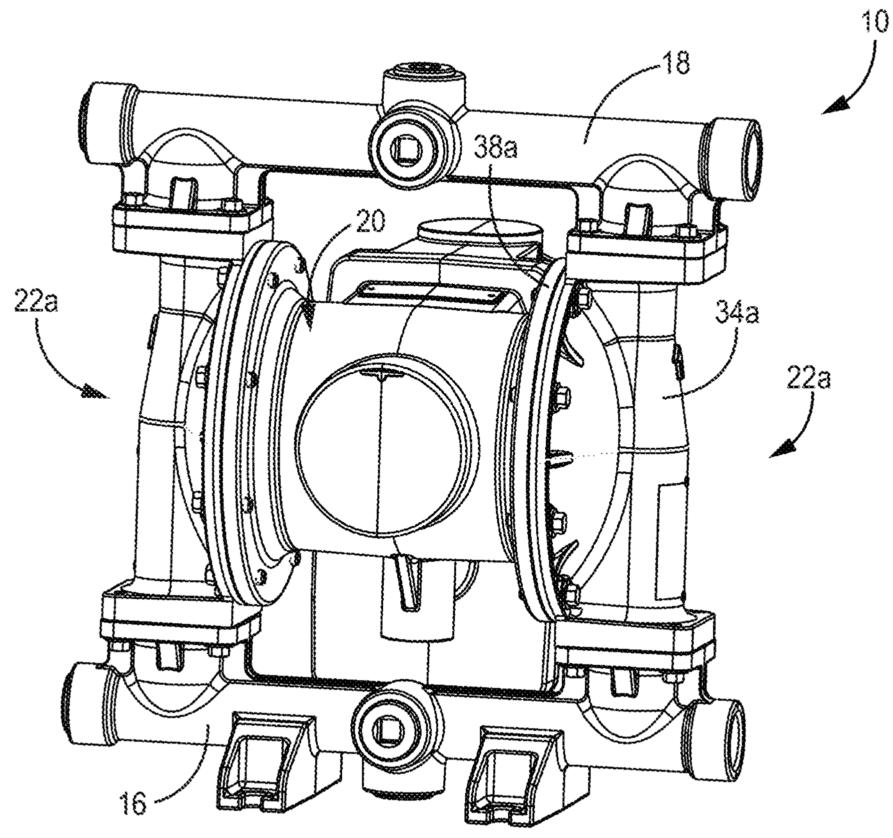
FIG. 4A is an isometric view of an electrically operated pumping assembly with a first fluid module mounted.
Figure 4B:
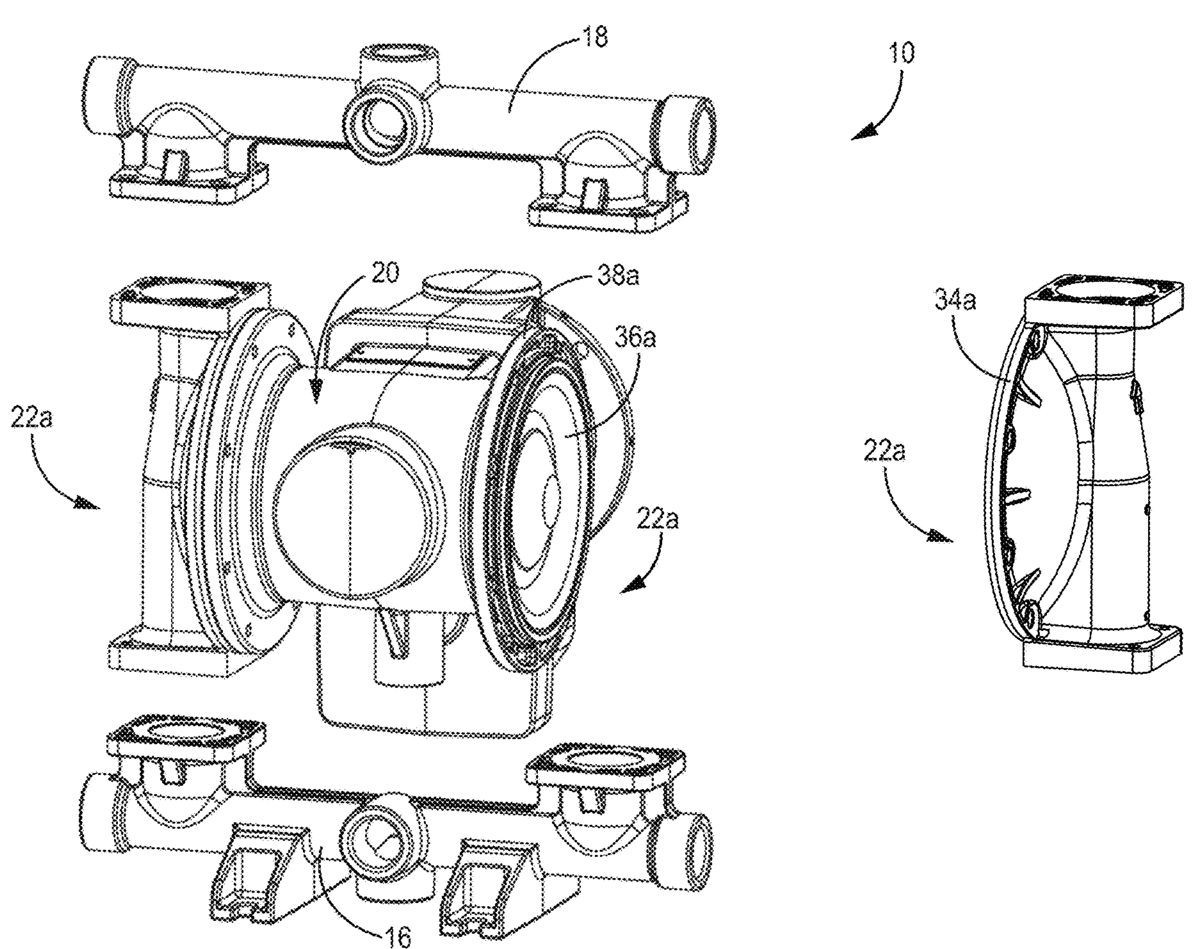
FIG. 4B is an isometric view of the electrically operated pumping assembly showing a first fluid manifold removed.

In FIG. 4A, pumping assembly 10 is shown with fluid modules 22*a* assembled to drive housing 20. In FIG. 4B, inlet manifold 16, outlet manifold 18, and fluid cover 34*a* are removed. Inlet manifold 16 and outlet manifold 18 are removed from fluid cover 34*a*. Fasteners, such as bolts, are released to remove inlet manifold 16 and outlet manifold 18. Fluid cover 34*a* is detached from adaptor 38*a* by removing fasteners 50*b*.

Figure 4C:
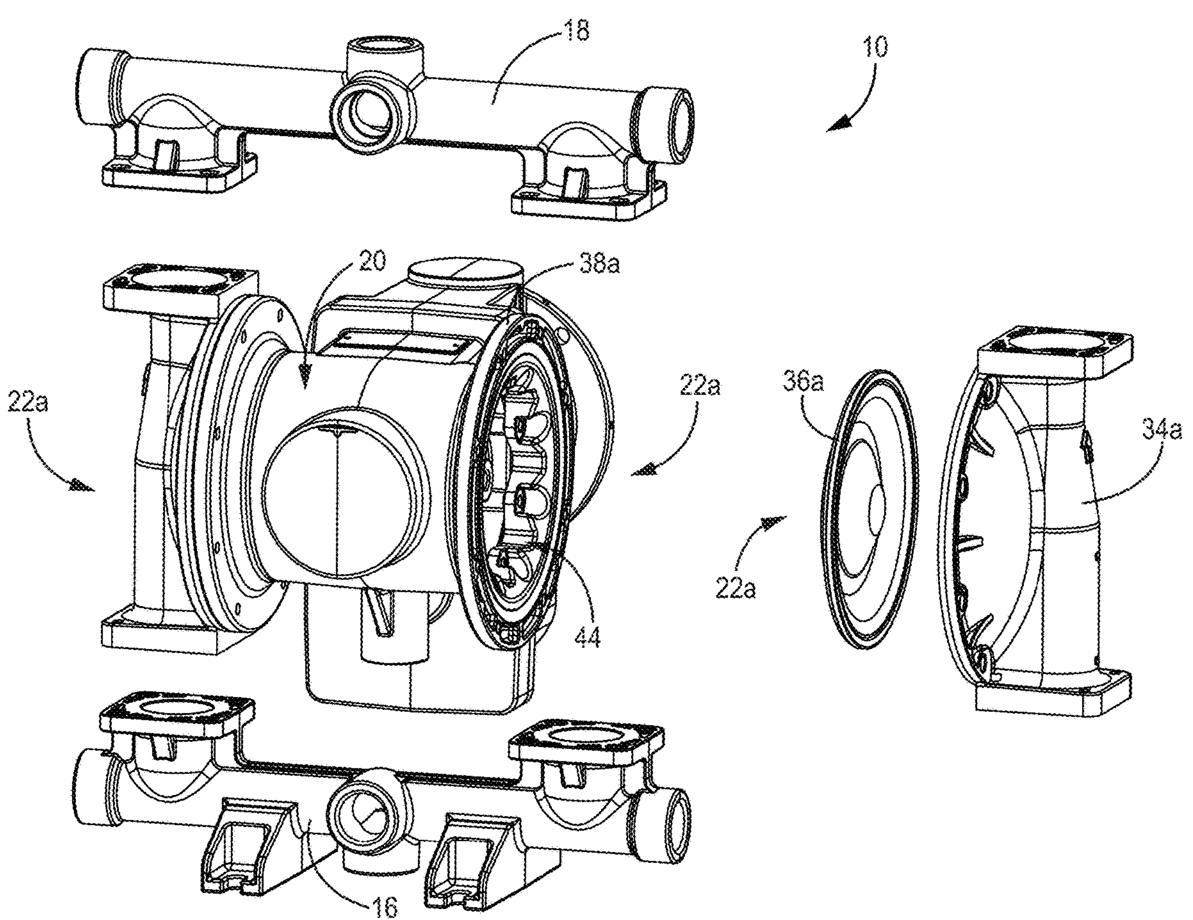
FIG. 4C is an isometric view of the electrically operated pumping assembly showing the first fluid manifold and a first diaphragm removed.

In FIG. 4C, diaphragm 36*a* is detached from drive 24 and removed. The diaphragm 36*a* can be removed by release of the connector 66, which may involve releasing parts of the connector 66 and/or diaphragm 36*a* which sandwich the center of the diaphragm 36*a*. For example, the connector 66 may be unthreaded from a diaphragm plate of the diaphragm 36*a*. In some examples, the diaphragm 36*a* can be rotated about pump axis P-P to disconnect diaphragm 36 from drive 24, such as by unthreading the connector 66 from bearing plate 46. With diaphragm 36*a* removed, fasteners 50*a* securing adaptor 38*a* to drive housing 20 are exposed. Components of drive 24 are also exposed through central aperture 44 of adaptor 38*a*. As discussed in more detail below, components of drive 24 can be accessed and serviced through central aperture 44 of adaptor 38*a*. In some examples of drive 24, components of drive 24 can be removed through central aperture 44 while adaptor 38*a* remains mounted to drive housing 20.

Figure 4D:
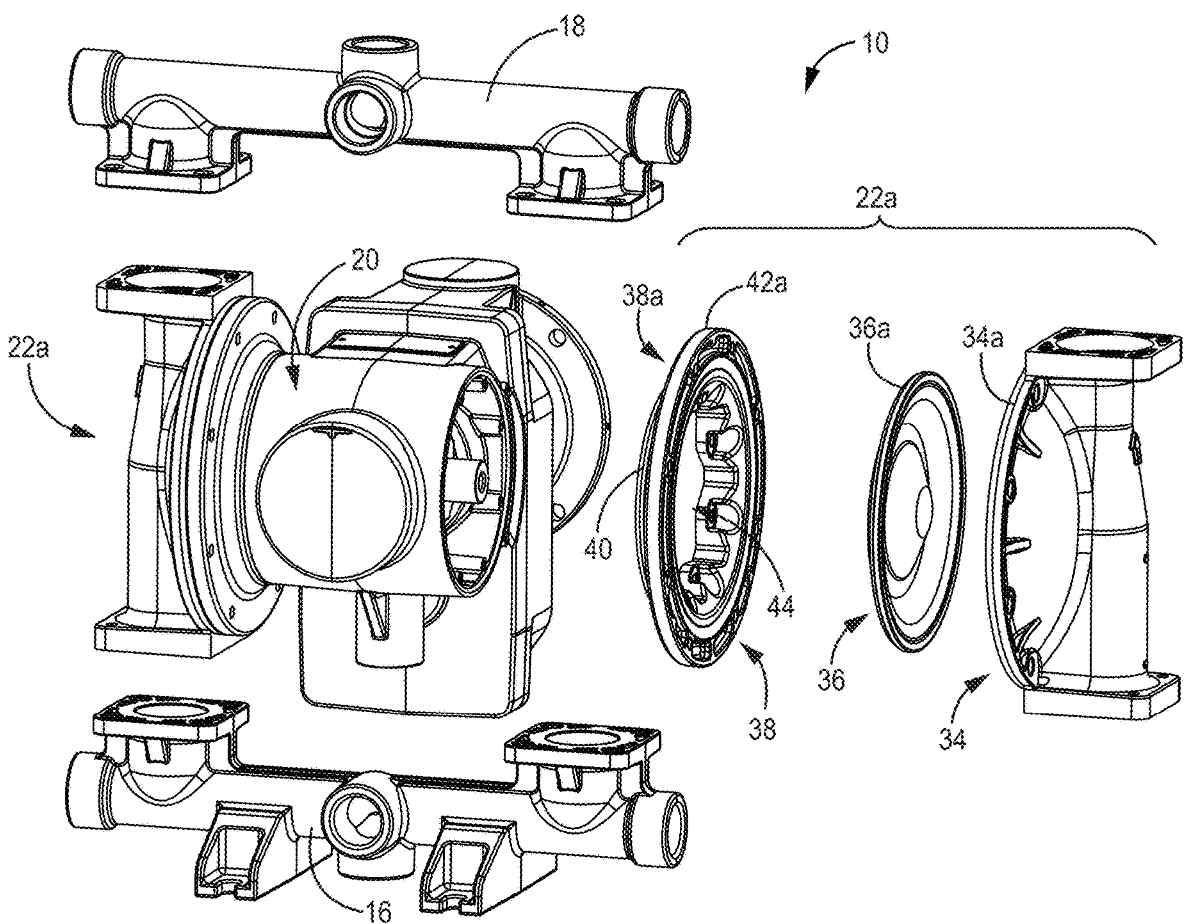
FIG. 4D is an isometric view of the electrically operated pumping assembly showing the first fluid manifold, the first diaphragm, and a first adaptor removed.

In FIG. 4D, adaptor 38*a* is detached from and removed from drive housing 20. Fasteners 50*a* are removed to release adaptor 38*a* from drive housing 20. Fasteners 50*a* are removed from inner mounting portion 40 and drive housing 20, disconnecting adaptor 38*a* from drive housing 20. Fluid module 22*a* is thereby removed from pump 14.

Figure 4E:
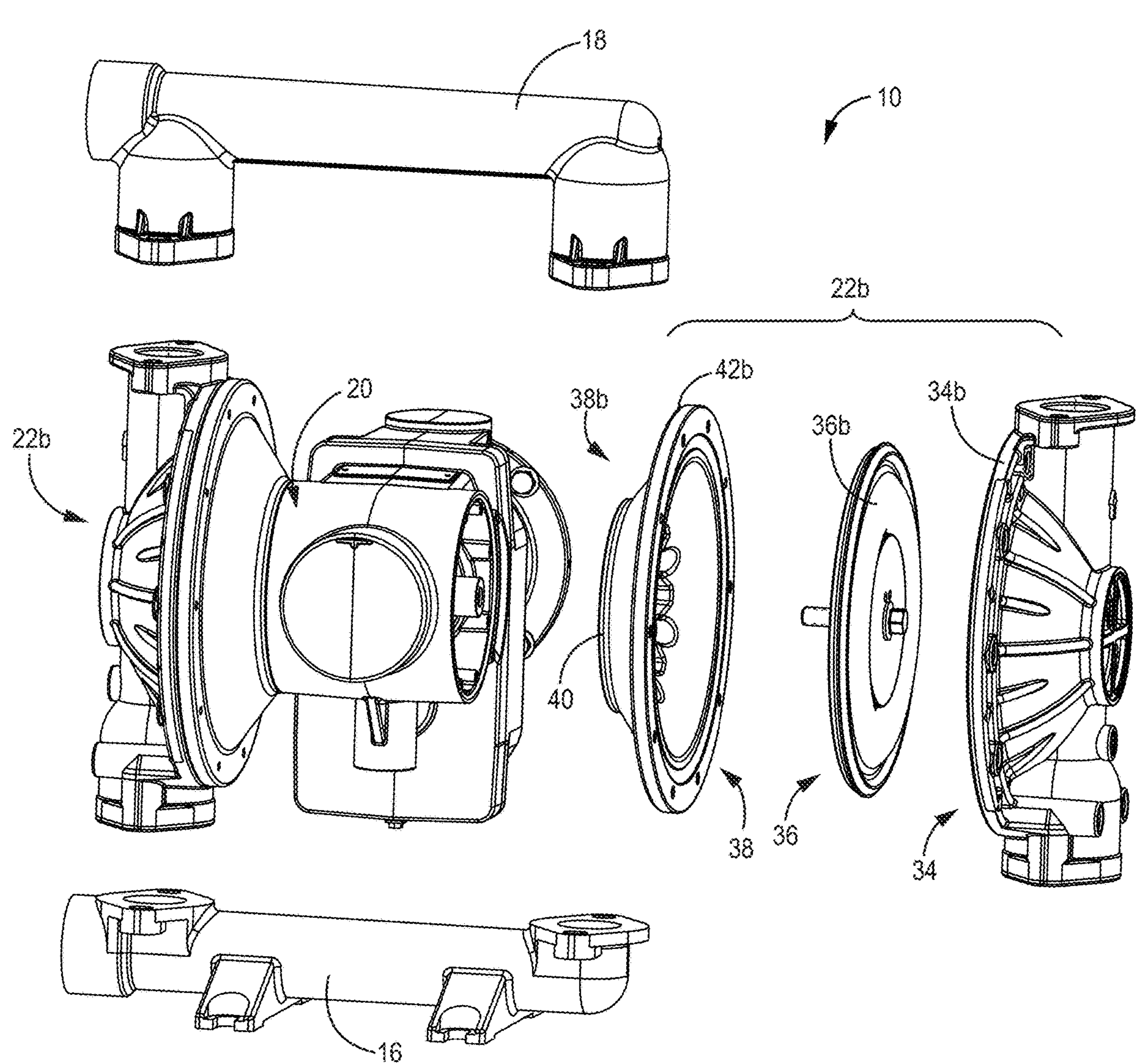
FIG. 4E is an isometric view of the electrically operated pumping assembly showing a second fluid manifold, second diaphragm, and second adaptor removed.

FIG. 4E shows the introduction of fluid module 22*b*. Fluid module 22*b* is different than, but similar to, fluid module 22*a*. Fluid module 22*b* includes like components to fluid module 22*a* except components of fluid module 22*b* are larger than those of fluid module 22*a*.

Figure 4F:
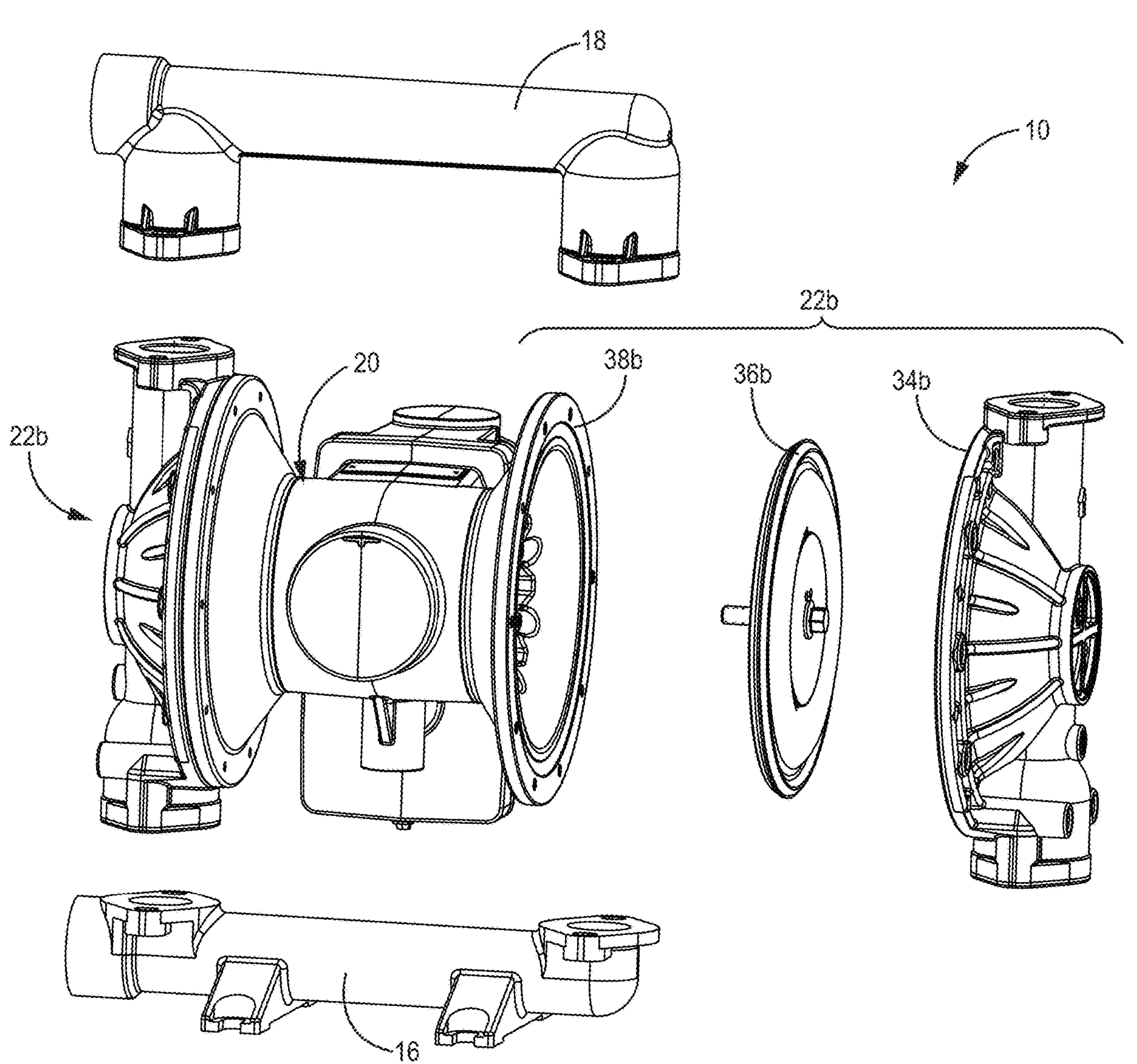
FIG. 4F is an isometric view of the electrically operated pumping assembly showing the second adaptor installed.

FIG. 4F shows adaptor 38*b* mounted to drive housing 20. Adaptor 38*b* includes inner mounting portion 40 and outer mounting portion 42*b*. Inner mounting portion 40 of adaptor

38*b* is configured to interface with and mount to drive housing 20 in the same manner as inner mounting portion 40 of adaptor 38*a*. Inner mounting portions 40 of each of adaptor 38*a* and adaptor 38*b* can have the same fastener opening configuration, the same diameters, and the same sealing faces. Adaptor 38*a* and adaptor 38*b* having inner mounting portions 40 of the same configuration facilitates mounting of the differently sized fluid module 22*a* and fluid module 22*b* to the same drive housing 20. Adaptor 38*b* can be mounted to drive housing 20 by fasteners 50*a*.

Figure 4G:
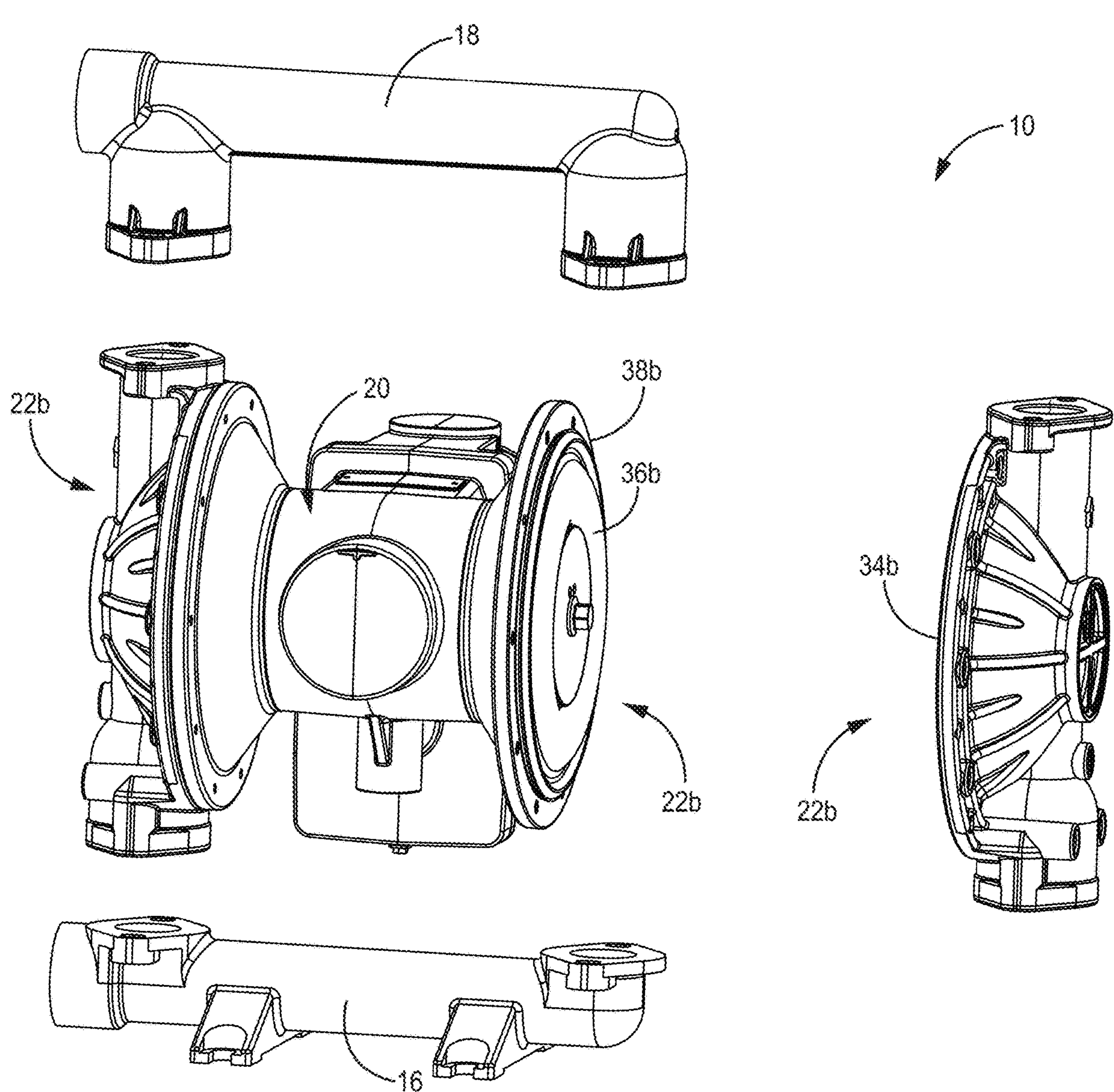
FIG. 4G is an isometric view of the electrically operated pumping assembly showing the second adaptor and the second diaphragm installed.

FIG. 4G shows diaphragm 36*b* connected to drive 24 and disposed in place relative adaptor 38*b*. Diaphragm 36*b* of fluid module 22*b* has a larger diameter than diaphragm 36*a* of fluid module 22*a*. The larger size of diaphragm 36*b* facilitates pump 14 displacing a larger volume of fluid for each stroke. Diaphragm 36*b* is mounted to drive 24 in the same manner as diaphragm 36*a* and driven by drive 24 in the same manner as diaphragm 36*a*.

Figure 4H:
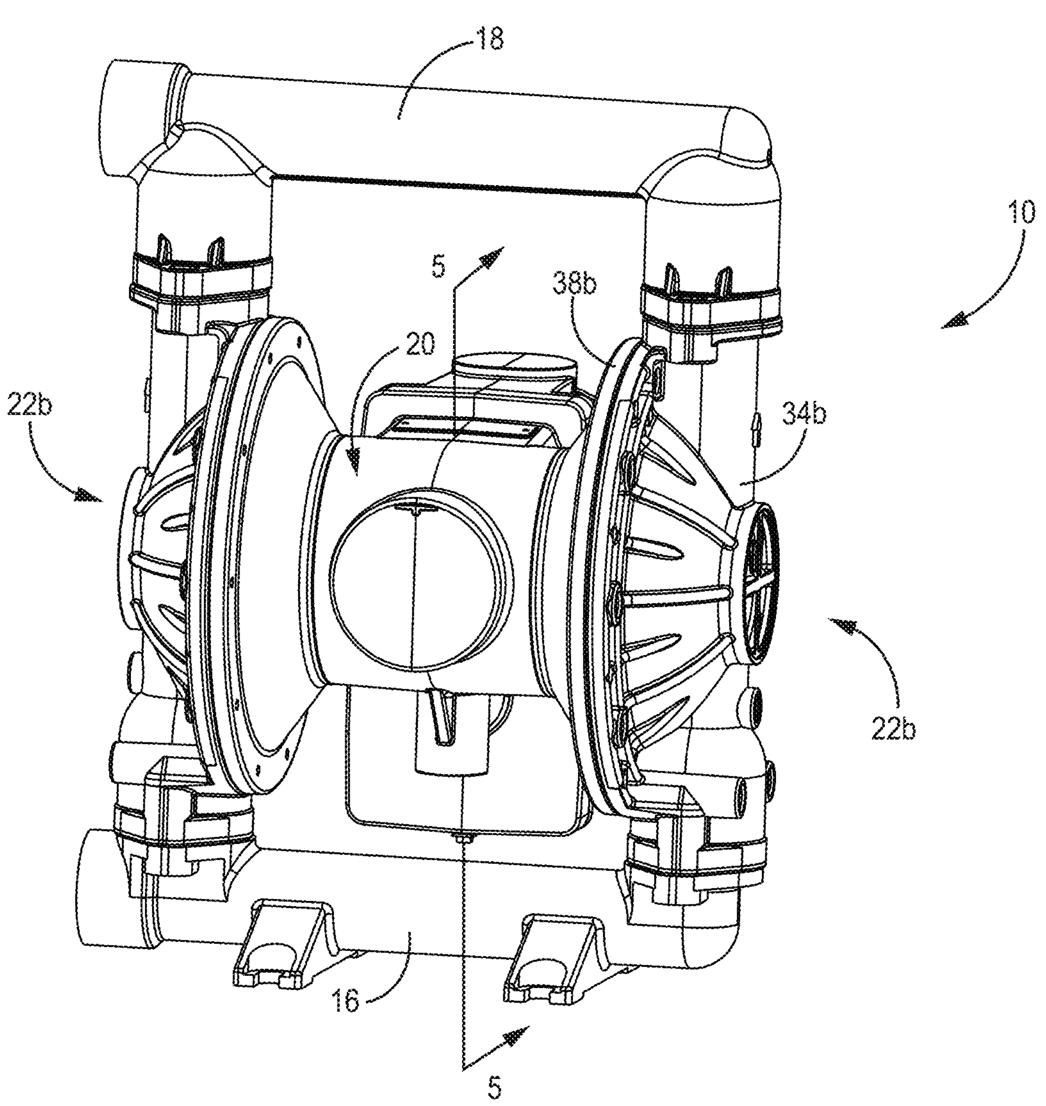
FIG. 4H is an isometric view of the electrically operated pumping assembly showing a second fluid module installed.

FIG. 4H shows fluid cover 34*b* mounted to adaptor 38*b* and inlet manifold 16 and outlet manifold 18 connected to fluid modules 22*b*. Fluid cover 34*b* is mounted to outer mounting portion 42*b* of adaptor 38*b*. Fluid cover 34*b* is placed over diaphragm 36*b* to capture diaphragm 36*b* between outer mounting portion 42*b* and fluid cover 34*b*. Fluid cover 34*b* can be mounted to outer mounting portion 42*b* by fasteners 50*b*. Outer mounting portion 42*b* has a larger diameter than outer mounting portion 42*a*. Fluid cover 34*b* has a larger diameter than fluid cover 34*a*. The larger diameters facilitate mounting of diaphragm 36*b* to cause the higher displacement per pump stroke.

Pumping assembly 10 provides significant advantages. Pumping assembly 10 has an electrically powered drive 24 that causes pumping by pump 14. The drive 24 and motor 12 are relatively costly components of pumping assembly 10. Pumping assembly 10 is modular and can be modified to output larger or smaller volumes of fluid per stroke. Each of fluid module 22*a* and fluid module 22*b* are configured to mount to drive housing 20. Each of diaphragm 36*a* and diaphragm 36*b* connect to and can be displaced by drive 24. Various fluid modules having different sizes and displacements can be mounted to the same drive housing 20 and powered by the same drive 24. As such, the user can have a single motor 12, drive 24, and drive housing 20 and can modify pumping assembly 10 by mounting fluid modules 22 having any desired size to provide any desired displacement to the drive housing 20.

The modular nature of pumping assembly 10 provides cost savings as the user is not required to purchase a different motor 12, drive 24, and drive housing 20 to obtain a different displacement and can instead mount different fluid modules 22. The modular nature of pumping assembly 10 also provides a space savings as the user is not required to store full pump assemblies 10 and can instead simply store various fluid modules 22, which require less storage space. The modular nature of pumping assembly 10 further provides for efficient changeover between pumps having various displacements. The other components of pumping assembly 10 can remain installed while the user swaps out fluid modules 22 to change the displacement of pump 14. The user does not have to manipulate and remove the entire motor 12, drive 24, and/or drive housing 20, providing savings in time and labor.

Figure 5:
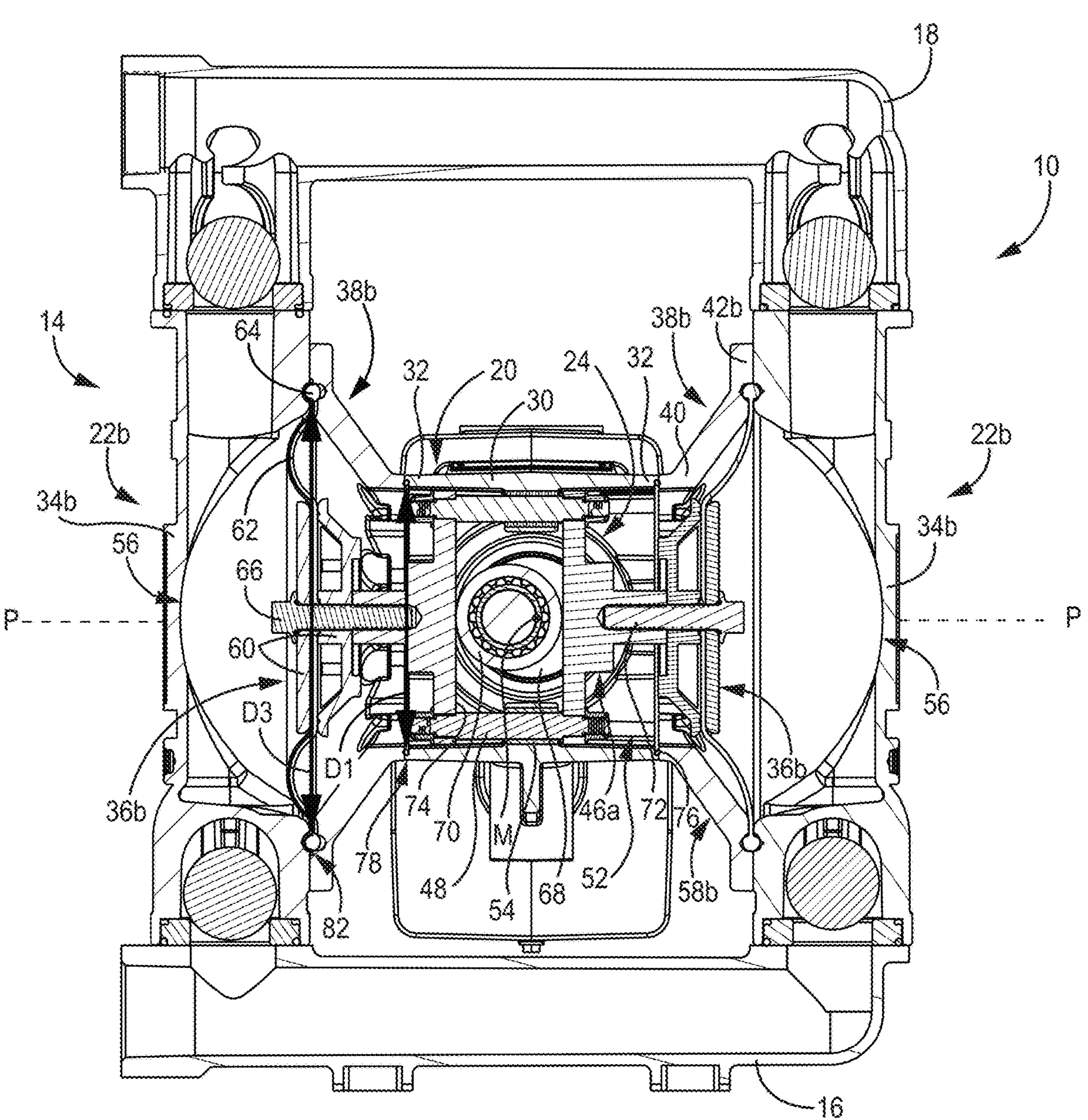
FIG. 5 is a cross-sectional view taken along line 5-5 in FIG. 4H.

FIG. 5 is a cross-sectional view taken along line 5-5 in FIG. 4H. Fluid modules 22*b* are mounted to drive housing 20. Fluid modules 22*b* are disposed coaxially on pump axis P-P.

Inner mounting portion 40 interfaces with drive housing 20 at first interface 78. Inner mounting portion 40 contacts end 32 of drive housing 20 at first interface 78. Inner mounting portion 40 seals with the end 32 of drive housing 20 with adaptor 38*b* mounted to drive housing 20. In the example shown, annular seal 76 is disposed between drive housing 20 and inner mounting portion 40. Inner mounting portions 40 of adaptors 38*b* have diameters D1 that are the same diameter as that of inner mounting portions 40 of adaptors 38*a*. The same diameters of inner mounting portion 40 of adaptor 38*b* and inner mounting portion 40 of adaptor 38*a* facilitates fluid module 22*b* mounting to the same drive housing 20, in the same manner, and at the same location as fluid module 22*b*.

Fluid covers 34*b* are disposed between and fluidly connected to inlet manifold 16 and outlet manifold 18. Fluid covers 34*b* are connected to outer mounting portions 42*b* of adaptors 38*b*. Fluid covers 34*b* contact outer mounting portion 42 at third interface 82. Diaphragms 36*b* are captured between fluid covers 34*b* and adaptors 38*b*. M ore specifically, circumferential edge 64 is captured between adaptor 38*b* and fluid cover 34*b*. Circumferential edge 64 can include a bead disposed within grooves formed in outer mounting portion 42*b* and fluid cover 34*b*. Circumferential edge 64 forms an annular seal between fluid cover 34*b* and outer mounting portion 42*b* at third interface 82. In the example shown, complimentary grooves are formed on each of outer mounting portion 42*b* and fluid cover 34*b* to receive circumferential edge 64.

Diaphragms 36*b* are connected to drive 24 and powered by drive 24 in the same manner as diaphragms 36*a*. Connectors 66 extend into mounting bores 72 formed in bearing plates 46*a* to fix bearing plates 46*a* to the centers of diaphragms 36*b*. Drive 24 can displace diaphragms 36 through each of the pressure stroke and the suction stroke.

Pumping assembly 10 with fluid modules 22*b* installed operates in the same manner as pumping assembly 10 with fluid modules 22*a* installed. Eccentric 68 rotates about axis M to drive bearing 70 in a circular path about axis M. Bearing 70 pushes on bearing plates 46*a* and rods 48 connect bearing plates 46*a* to simultaneously displace diaphragms 36*b* in one of the first axial direction AD1 and second axial direction AD2.

Transition portion 58*b* extends between and connects inner mounting portion 40 and outer mounting portion 42*b*. Transition portion 58*b* increases the diameter of adaptor 38*b* between the diameter D1 of inner mounting portion 40 and the diameter D3 of outer mounting portion 42*b*. Diameter D3 is larger than diameter D2. The larger diameter D3 of outer mounting portion 42*b* relative to the diameter D2 of outer mounting portion 42*a* facilitates use of the larger diaphragm 36*b* to generate higher flow. Diaphragm 36*b* has a diameter larger than a diameter of diaphragm 36*a*. The process discussed can also be utilized to mount a diaphragm having a smaller relative diameter to generate higher pressures and/or lower flow.

It is contemplated that a variety of sizes of fluid modules 22 can be connected to the same drive housing 20. For example, ten different sizes having different diaphragm diameters can alternately be attached to the same drive housing 20 and driven by the same drive 24. Each of the different sized fluid modules 22 is able to attach to the same end 32 of drive housing 20 at the same first interface 78 by the respective adaptor 38 of each fluid module 22 having the same fastener hole pattern and spacing to interface with the fastener holes of the drive housing 20, yet each adaptor 38 can have a different size outer mounting portion 42 (e.g., different diameter) to accommodate the different sizes of diaphragms 36. In this way, the adaptors 38 adapt between the single size of the first interface 78 with drive housing 20 and multiple different diaphragm configurations.

Figure 6A:
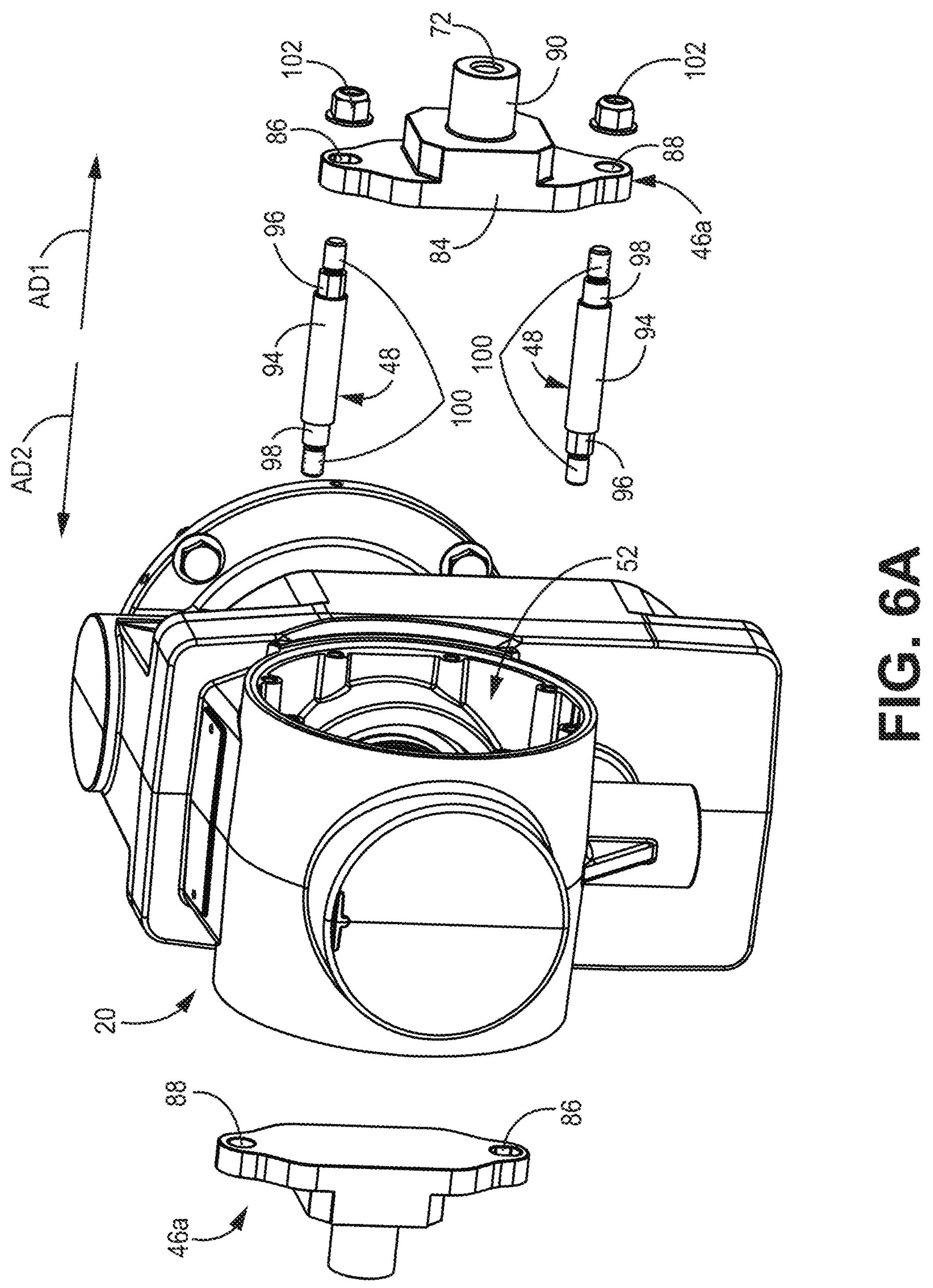
FIG. 6A is an exploded isometric view showing an electrically operated pumping assembly with fluid modules removed and parts of a first drive exploded from the drive housing.
Figure 6B:
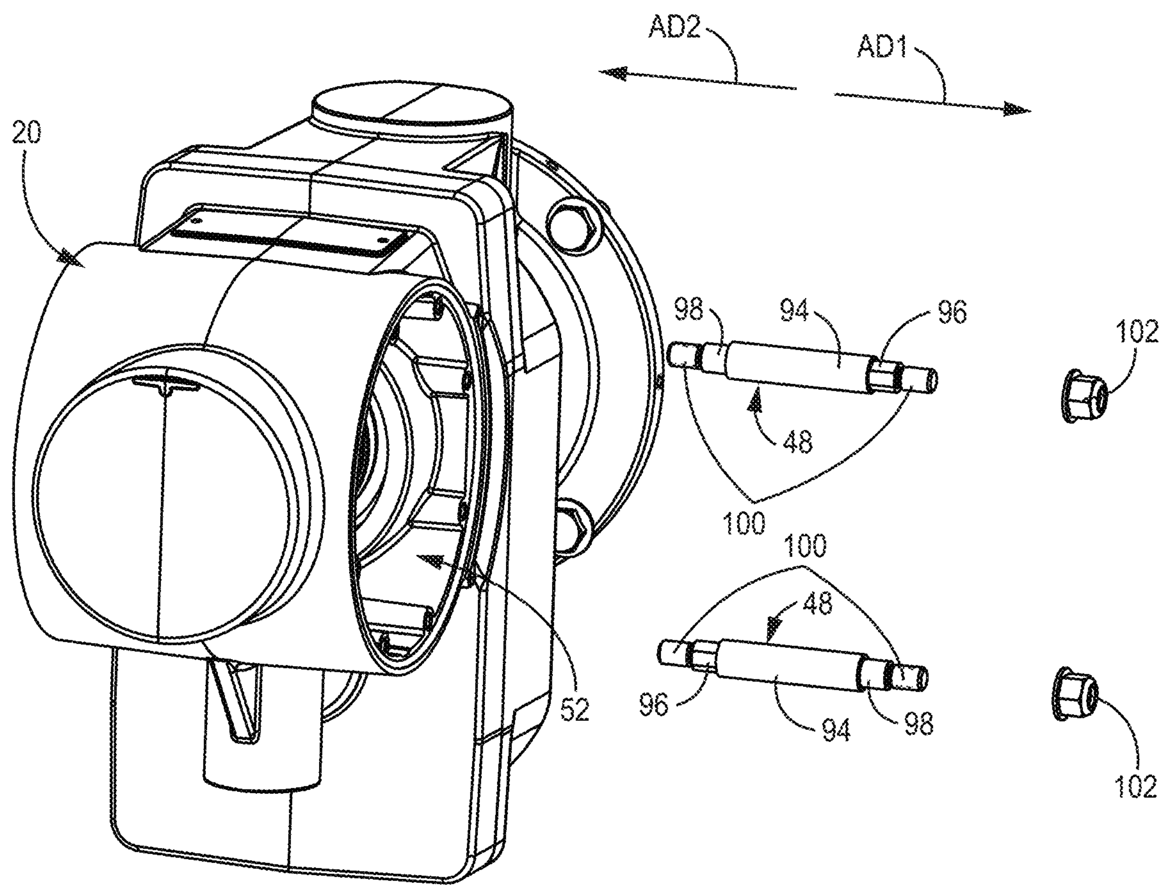
FIG. 6B is an exploded isometric view showing the electrically operated pumping assembly with parts of the first drive removed.
Figure 6C:
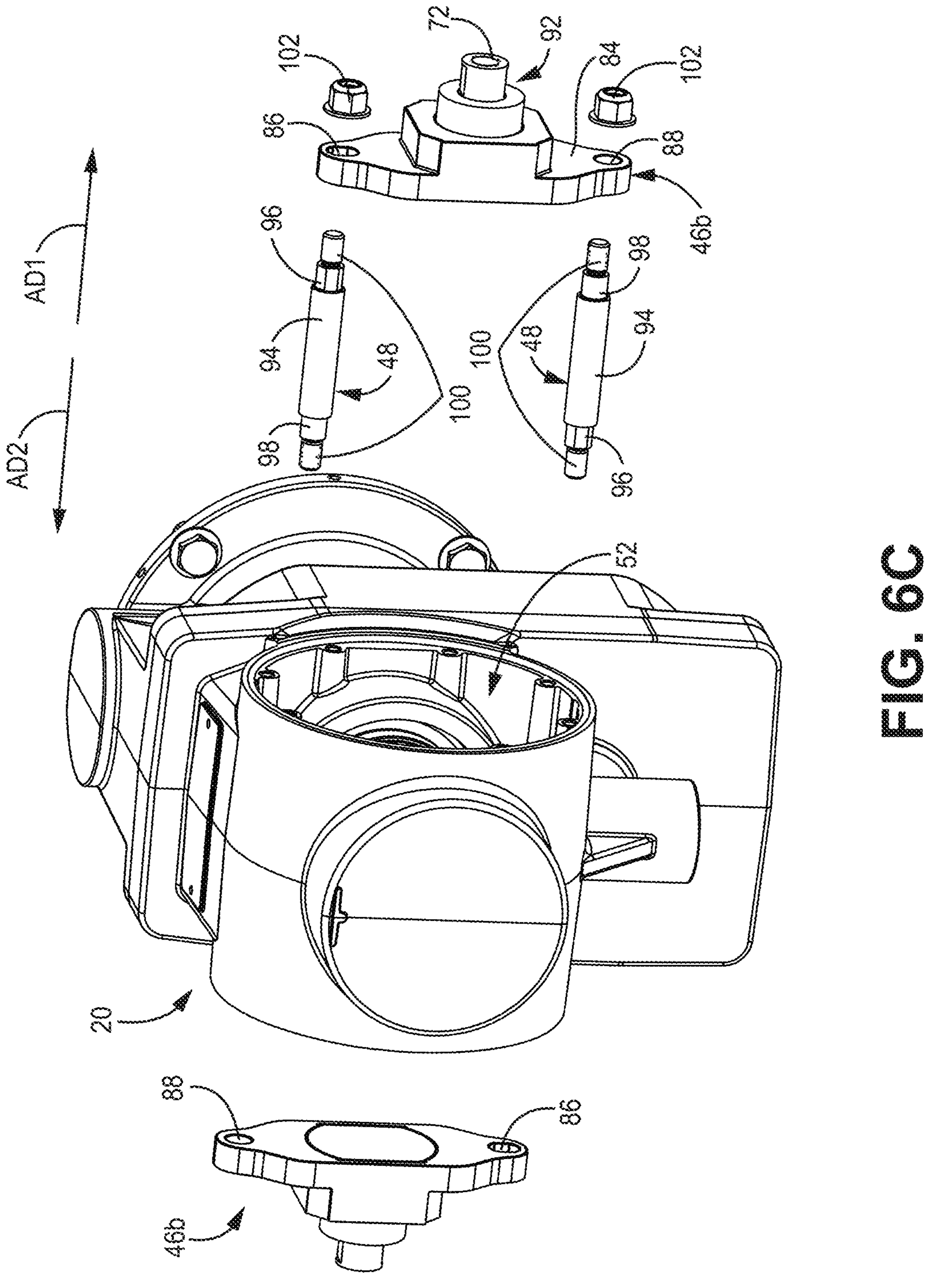
FIG. 6C is an exploded isometric view showing the electrically operated pumping assembly with parts of a second drive exploded from the drive housing.

FIGS. 6A-6C show a process of removing drive components configured to displace the diaphragms 36 through both pumping and suction strokes and replacing those drive components with drive components configured to displace diaphragms 36 through the suction stroke while working fluid within drive chamber 52 displaces the diaphragms 36 through a pumping stroke.

The drive 24 including bearing plates 46*a* is configured to drive the diaphragms 36 through both the suction and the pumping strokes. However, the pump 14 can be adapted so that the drive 24 moves the diaphragms 36 only through the suction strokes while the diaphragms 36 are then pneumatically or hydraulically pushed through the pumping strokes. The benefit of such a configuration is that the output pressure of the pump 14 will be at or near the pneumatic or hydraulic pressure that pushes on the diaphragms 36, whereas only mechanical pushing through both the pumping and suction strokes can result in pressure spikes, particularly in deadhead conditions. FIGS. 6A-6C demonstrate the conversion of the drive 24.

Each bearing plate 46*a* includes plate body 84, mounting bore 72, first receiving opening 86, and second receiving opening 88. Mounting bore 72 is formed in static projection 90. Each bearing plate 46*b* includes plate body 84, mounting bore 72, first receiving opening 86, and second receiving opening 88. Mounting bore 72 is formed in pull 92. Rods 48 include rod body 94 extending between contoured end 96 and cylindrical end 98.

In FIG. 6A, bearing plates 46*a* and rods 48 have been removed from drive housing 20. Bearing plates 46*a* are shown in the inverse orientation relative each other. The bearing plate 46*a* to the left of drive housing 20 in the view of FIG. 6A is oriented such that first receiving opening 86 is at a lower end of plate body 84 and second receiving opening 88 is at a top end of plate body 84. The bearing plate 46*a* to the right of drive housing 20 in the view of FIG. 6A is oriented such that first receiving opening 86 is at a top end of plate body 84 and second receiving opening 88 is at a lower end of plate body 84.

Similar to bearing plates 46*a*, rods 48 are oriented inverse each other. The upper one of rods 48 shown is oriented with contoured end 96 facing in first axial direction AD1 to be received by first receiving opening 86 of the bearing plate 46*a* spaced in first axial direction AD1 from drive housing 20. Cylindrical end 98 of the upper one of rods 48 is facing in second axial direction AD2 to be received by second receiving opening 88 of the bearing plate 46*a* spaced in second axial direction AD2 from drive housing 20. The lower one of rods has contoured end 96 facing in second axial direction AD2 and cylindrical end 98 facing in first axial direction AD1.

Contoured end 96 is configured to extend into first receiving opening 86. Contoured ends 96 include a contour configured to mate with a contour of first receiving opening 86. The mating contours prevent rod 48 from rotating relative bearing plate 46*a*, 46*b*. For example, contoured ends 96 can include flats and first receiving openings 86 can be slots configured to mate with the flats. Contoured end 96 can be partially cylindrical and partially flat. In addition, the slot forming first receiving opening 86 can be vertically larger than contoured end 96. The interface between contoured end 96 and first receiving opening 86 provides vertical play during assembly into drive housing 20 to allow rods 48 to properly mount within rod sleeves 54. Cylindrical end 98 extends into second receiving opening 88. Contoured end 96 and cylindrical end 98 have reduced diameters relative rod body 94.

Extensions 100 project axially from each of contoured end 96 and cylindrical end 98. With rods 48 interfacing with bearing plates 46*a*, 46*b*, extensions 100 are disposed on opposite axial sides of plate body 84 from rod body 94. Extensions 100 are removably connected to locks 102 to secure rods 48 to bearing plates 46*a*. In the example shown, extensions 100 are threaded shafts and locks 102 are nuts configured to threadingly engage mounting extensions. It is understood, however, that extensions 100 and locks 102 can interface in any manner suitable for securing rod 48 to bearing plate 46*a*, 46*b*. Only one pair of locks 102 are shown, but it is understood that a pair of locks 102 is utilized to secure the pair of rods 48 to each bearing plate 46*a*, 46*b*.

During disassembly, locks 102 are removed from extensions 100 and bearing plates 46*a*, 46*b* are pulled axially away from drive housing 20. In some examples, the locks 102 associated with one of bearing plates 46*a*, 46*b* are removed and then the rods 48 and other bearing plate 46*a*, 46*b* can be removed while still assembled together. Rods 48 are disconnected from bearing plates 46.

In FIG. 6B, bearing plates 46*a* have been removed. In FIG. 6C, bearing plates 46*b* are introduced. As discussed further below, bearing plates 46*b* have a different configuration than bearing plates 46*a*. Rods 48 are connected to bearing plates 46*b* and locked to bearing plates 46*b* by locks 102. In some examples, contoured ends 96 are inserted into first receiving openings 86 and secured such that each bearing plate 46*b* has an associated rod 48 extending from it. Each bearing plate 46*b* and its rod 48 can then be inserted into drive housing 20 such that cylindrical ends 98 extend into second receiving openings 88 of the other bearing plate 46*b*.

The carriage formed by bearing plates 46*a* and rods 48 or bearing plates 46*b* and rods 48 can be converted between different configurations within the same drive housing 20 and the different configurations are powered by the same motor 12. Pumping assembly 10 provides significant advantages by facilitating the user switching between configurations by changing components of drive 24 without replacing the full pumping assembly 10.

Figures 7A, 7B, 7C:
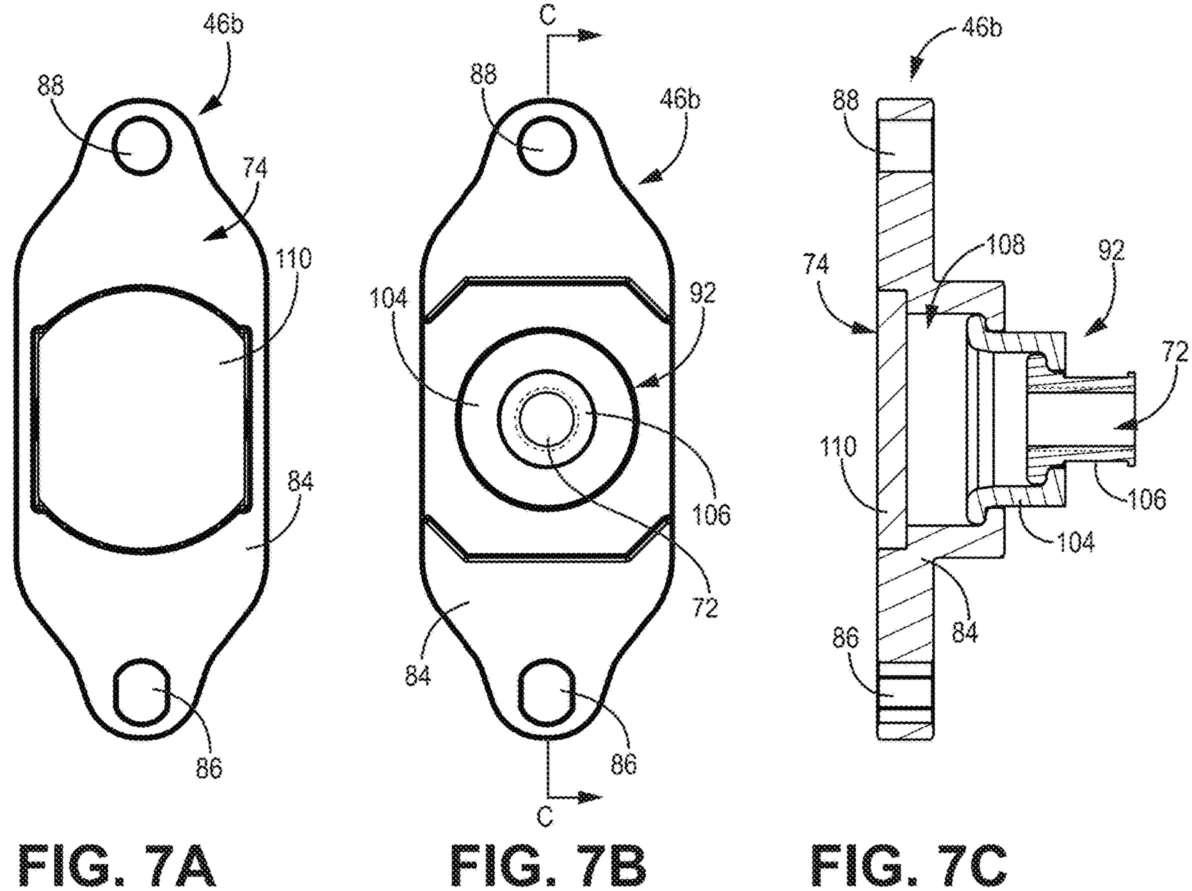
FIG. 7A is a rear elevation view of a second bearing shown in FIG. 6C.
FIG. 7B is a front elevation view of the second bearing plate shown in FIG. 7A.
FIG. 7C is a cross-sectional view taken along line C-C in FIG. 7B.

FIG. 7A is a rear elevation view of bearing plate 46*b*. FIG. 7B is a front elevation view of bearing plate 46*b*. FIG. 7C is a cross-sectional view taken along line C-C in FIG. 7B. FIGS. 7A-7C will be discussed together. Bearing plate 46*b* includes plate body 84, mounting bore 72, first receiving opening 86, and second receiving opening 88. Mounting bore 72 is formed in pull 92. Pull 92 includes inner section 104 and outer section 106. Plate body 84 defines pull chamber 108 and includes cover plate 110 enclosing pull chamber 108 and at least partially forming bearing surface 74.

Pull 92 is at least partially disposed within pull chamber 108. Inner section 104 includes an outwardly extending flange configured to mate with an inwardly extending flange to retain inner section 104 at least partially within pull chamber 108. Outer section 106 includes an outwardly extending flange configured to mate with an inwardly extending flange to retain outer section 106 at least partially within inner section 104. Inner section 104 and outer section 106 are each movable relative to plate body 84 and relative to each other. Mounting bore 72 is formed in outer section 106.

Pull 92 is configured such that bearing plate 46*b* can exert a tensile pulling force on diaphragm 36 to pull diaphragm 36 through a suction stroke. Inner section 104 and outer section 106 form a series of telescopic parts that prevent bearing plate 46*b* from driving the diaphragm 36 through a pumping stroke. Pull 92 can collapse into pull chamber 108 to prevent bearing plate 46*b* from driving diaphragm 36 through a pumping stroke.

Figure 8:
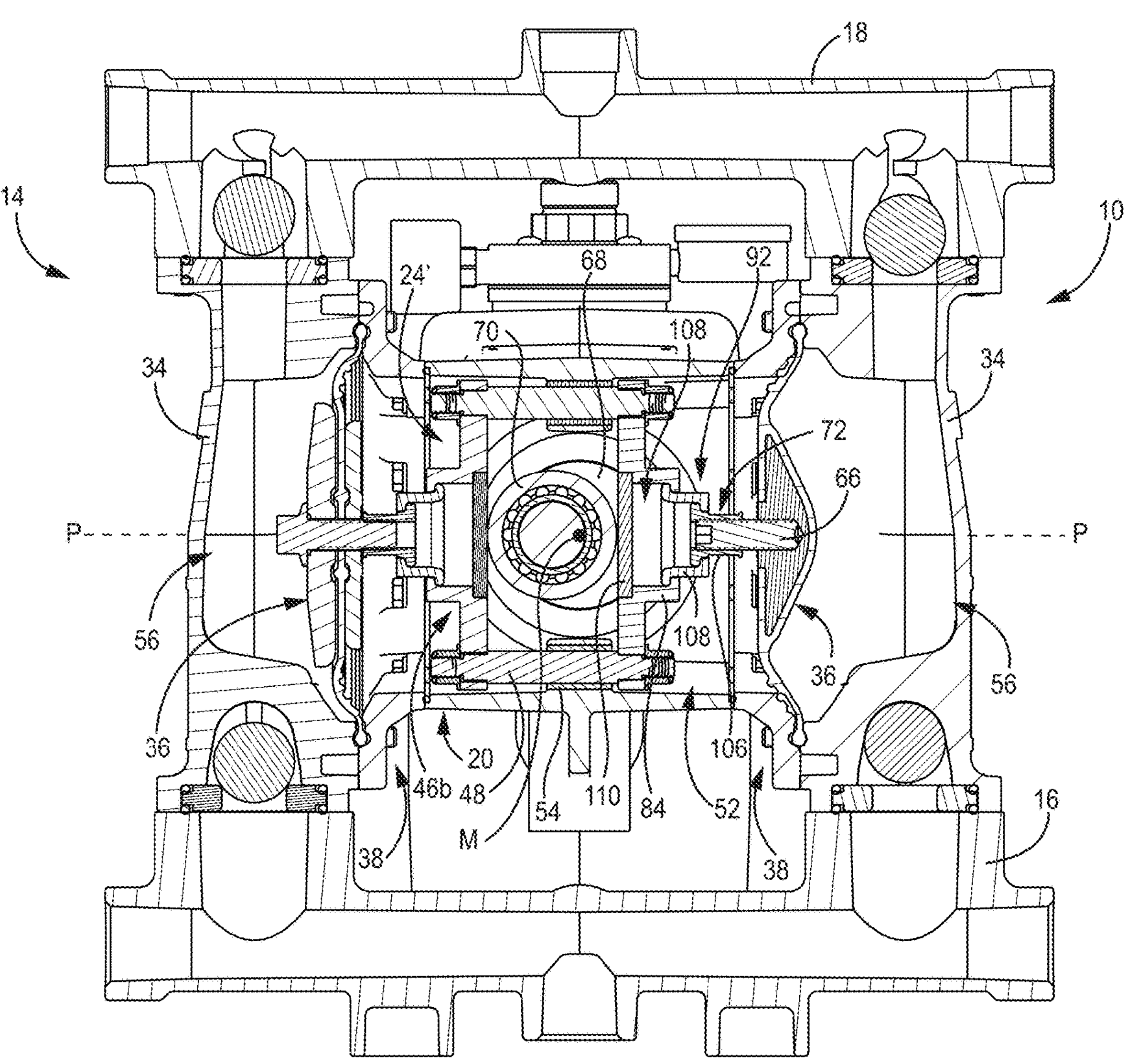
FIG. 8 is a cross-sectional view of an electrically operated pumping assembly having the second bearing plates shown in FIGS. 7A-7C.

FIG. 8 is a cross-sectional view of pumping assembly 10 with drive 24' including bearing plates 46*b* assembled within drive housing 20. In this configuration, drive chamber 52 is pressurized with a working fluid to charge drive chamber 52. For example, drive chamber 52 can be pressurized with compressed air or hydraulic fluid. Drive chamber 52 is fluidly sealed to prevent leakage of the working fluid from drive chamber 52. A single charge of working fluid can provide pumping force over multiple pump cycles. The working fluid is not exhausted between pump cycles. The charge pressure of the working fluid corresponds to the pumping pressure output by pump 14.

During operation, eccentric 68 causes bearing 70 to rotate about axis M to move the bearing plates 46*b* in a reciprocating manner in the first axial direction AD1 and second axial direction AD2. Pull 92 is connected to connector 66 of diaphragm 36. Pull 92 allows the bearing plate 46*b* to pull the connector 66 connected to outer section 106 toward the center of the drive housing 20, corresponding to the suction stroke. As the bearing 70 reverses axial direction to push the bearing plate 46*b* through the pumping stroke, pull 92 can collapse in a telescopic manner within pull chamber 108. Outer section 106 can collapse within inner section 104. Both outer section 106 and inner section 104 can collapse within pull chamber 108. Bearing plate 46*b* does not convey mechanical pumping force via the connector 66 to the diaphragm 36. Instead, the working fluid within the drive chamber 52 pushes on the inner side of the diaphragm 36 to move the diaphragm 36 through the pumping stroke. While telescopic pull 92 is shown herein, other pull 92 options are possible, such as belts (e.g., chains, ropes, tendons, etc.) which can convey a pulling force but not a pushing force similar to the telescopic pull 92 shown.

Drive 24' is configured to displace diaphragms 36 through respective suction strokes. Drive 24' is prevented from displacing diaphragms 36 through respective pumping strokes by pulls 92 and bearing plates 46*b*. Instead, the working fluid charging drive chamber 52 is used to provide the force on the diaphragm 36 to drive diaphragm 36 through the pumping stroke.

As discussed with regard to FIGS. 6A-8, pumping assembly 10 can be converted from having a purely mechanical drive 24 to a hybrid drive 24'. The mechanical drive 24 mechanically displaces diaphragms 36 through each of the pumping stroke and the suction stroke. The hybrid drive 24' mechanically displaces diaphragms 36 through the suction stroke and fluidically (e.g., pneumatically or hydraulically) displaces diaphragms 36 through the pumping stroke. The same drive housing 20 and motor 12 can be utilized with both the purely mechanical configuration and the hybrid configuration. The modular nature of pumping assembly 10 provides flexibility to the user, increases efficiency, and reduces costs. It is understood that hybrid drive 24' can be utilized with any desired motor. For example, pulls 92 or other pulling options can be utilized with the arrangement shown in FIG. 3B where motor 12' is fully within drive housing 20.

Figures 9A, 9B, 9C:
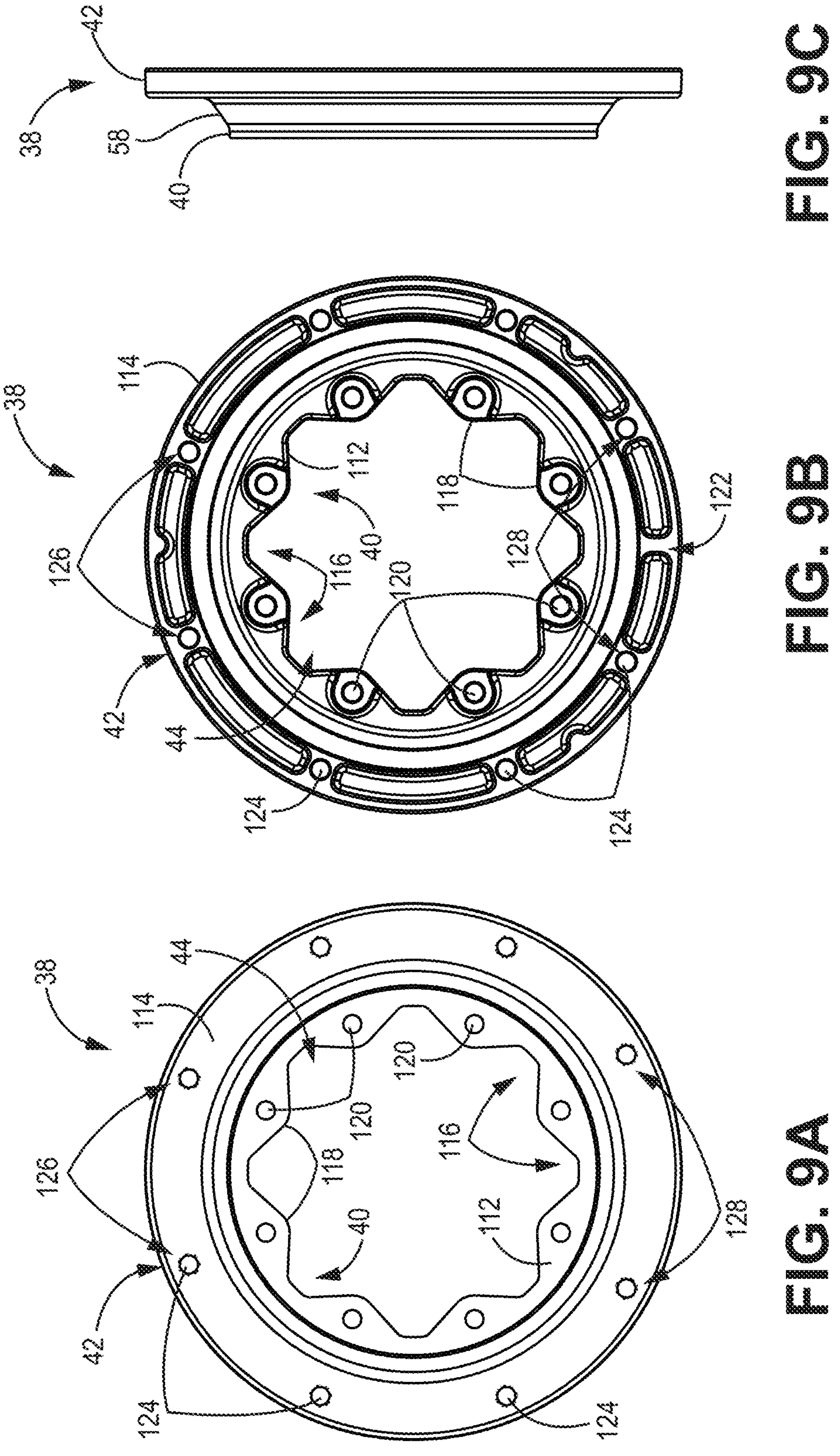
FIG. 9A is a front elevation view of an adaptor.
FIG. 9B is a rear elevation view of the adaptor.
FIG. 9C is a side elevation view of the adaptor.

FIG. 9A is a rear elevation view of adaptor 38. FIG. 9B is a front elevation view of adaptor 38. FIG. 9C is a side elevation view of adaptor 38. FIGS. 9A-9C will be discussed together. Adaptor 38 is substantially similar to adaptor 38*a* and adaptor 38*b*. Adaptor 38 includes inner mounting portion 40, outer mounting portion 42, central aperture 44, and transition portion 58. Inner mounting portion 40 includes inner ring 112 and outer mounting portion 42 includes outer ring 114. Inner ring 112 includes voids 116, projections 118, and inner holes 120. Outer ring 114 includes indicator 122 and outer holes 124. Outer holes 124 include first subset 126 and second subset 128.

Inner mounting portion 40 is disposed at a first end of transition portion 58 and outer mounting portion 42 is disposed at a second end of transition portion 58. Transition portion 58 increases the diameter of adaptor 38 between the smaller diameter of inner mounting portion 40 and the larger diameter of outer mounting portion 42. Central aperture 44 extends fully through adaptor 38.

Inner ring 112 projects radially inward relative transition portion 58. Inner ring 112 projects radially inward from a location where inner mounting portion 40 interfaces with and seals against end 32 of drive housing 20. Voids 116 are disposed between projections 118. Projections 118 are disposed between voids 116. Inner holes 120 extend through projections 118 and are evenly arrayed about inner ring 112. Inner holes 120 are disposed radially inward of the seal between inner mounting portion 40 and drive housing 20. Inner holes 120 are evenly spaced about inner ring 112. Inner holes 120 are symmetric about inner ring 112. Inner holes 120 are configured to align with housing holes 130 (FIG. 10C) formed in end 32 of drive housing 20. Fasteners, such as fasteners 50*a*, can extend through inner holes 120 and housing holes 130 to mount adaptor 38 to drive housing 20. Inner holes 120 are evenly arrayed about inner ring 112 such that adaptor 38 can mount to drive housing 20 in any desired orientation. Any one of inner holes 120 can be aligned with any one of housing holes 130 to mount adaptor 38 to drive housing 20. As such, adaptor 38 can be mounted at any desired clocked orientation relative to drive housing 20.

Outer ring 114 projects radially outward relative transition portion 58. Outer ring 114 projects radially outward from a location where outer mounting portion 42 interfaces with diaphragm 36 to form a seal between outer ring 114 and fluid cover 34. Outer holes 124 extend through outer ring 114 and are configured to align with cover holes 132 (FIGS. 12A-13A) through fluid cover 34. Outer holes 124 are disposed radially outward of the seal between outer mounting portion 42 and fluid cover 34. Fasteners, such as fasteners 50*b*, can extend through aligned ones of outer holes 124 and cover holes 132 to mount fluid cover 34 to adaptor 38. Unlike inner holes 120 that are evenly arrayed about inner ring 112, outer holes 124 are not evenly arrayed about outer ring 114. At least some of outer holes 124 have asymmetric spacing. First subset 126 of outer holes 124 have a first spacing therebetween and second subset 128 of outer holes 124 have a second spacing therebetween. The first spacing is different from the second spacing. In the example shown, the outer holes 124 forming first subset 126 are spaced closer together than the outer holes 124 forming second subset 128. The difference in the spacing provides mistake-proofing that ensures fluid module 22 is properly aligned to pump fluid, as discussed further herein. The uneven spacing between outer holes 124 prevents fluid cover 34 from being mounted to adaptor 38 in an incorrect orientation.

Indicator 122 is disposed on outer ring 114. In the example shown, indicator 122 is formed between second subset 128. Indicator 122 is formed on a portion of outer ring 114 that is easily visible by the user with adaptor 38 installed on drive housing 20. Indicator 122 shows the proper orientation of fluid cover 34 relative adaptor 38 to align outer holes 124 and cover holes 132 such that fluid cover 34 can mount to adaptor 38. Indicator 122 can be of any desired form for informing the user of the proper orientation of adaptor 38. For example, indicator 122 can be a bump, notch, gap, projection, symbol, difference in coloring, etc. suitable for indicating the proper orientation of adaptor 38.

Figure 10A:
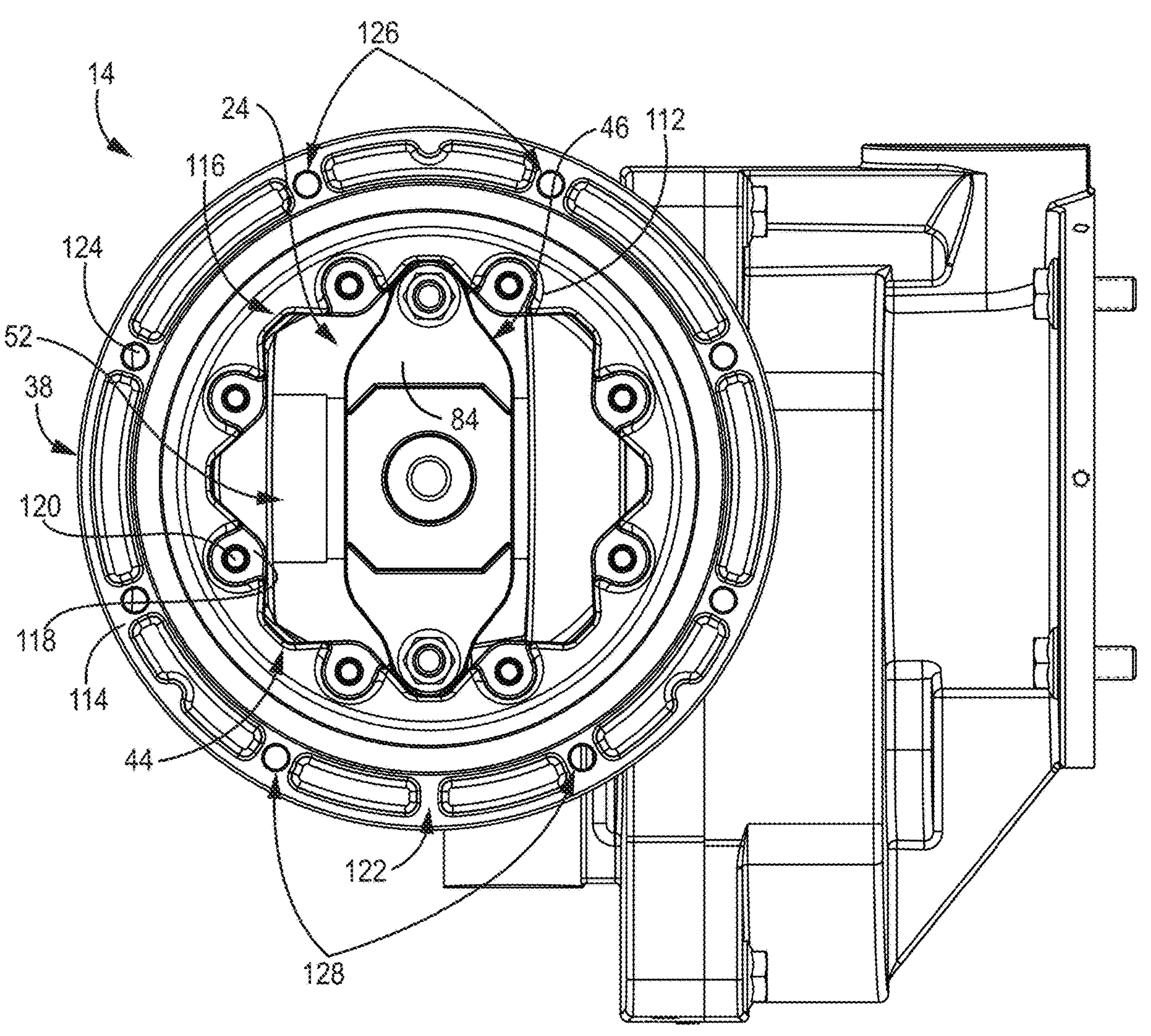
FIG. 10A is a side elevation view of an electrically operated pumping assembly with a fluid cover and diaphragm removed.
Figure 10B:
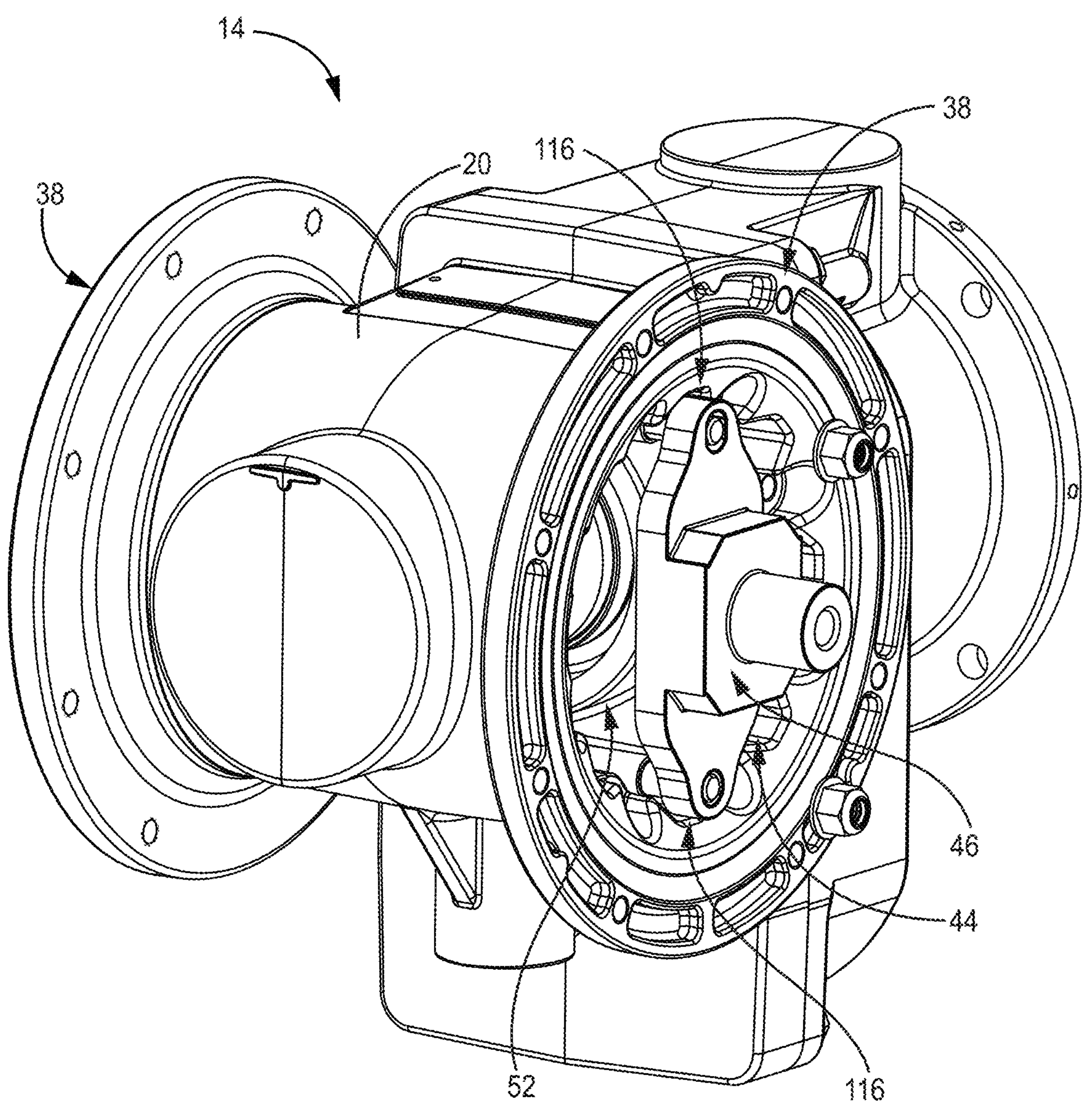
FIG. 10B is an isometric view of the electrically operated pumping assembly showing removal of bearing plates through the adaptor.
Figure 10C:
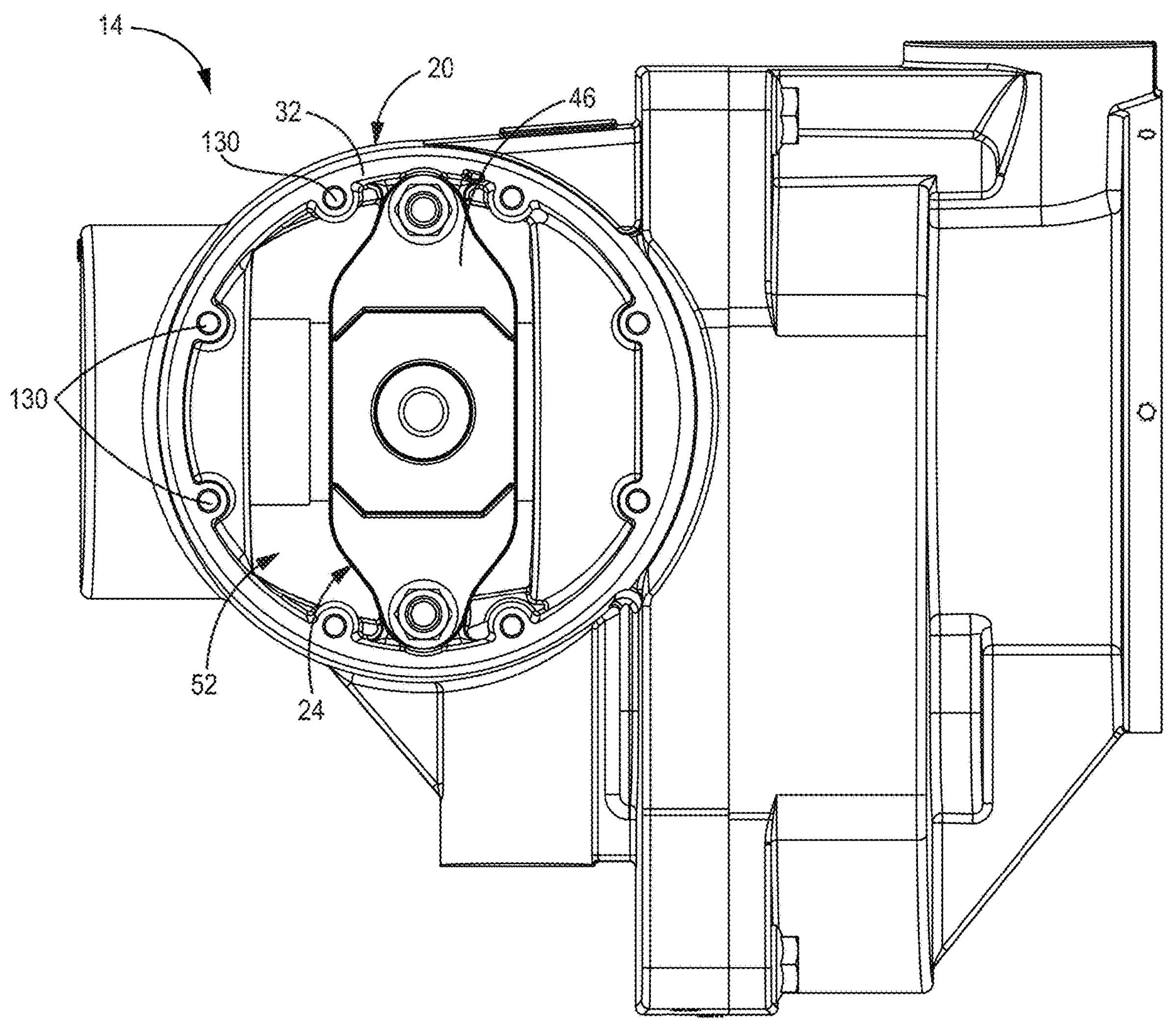
FIG. 10C is a side elevation view of the electrically operated pumping assembly with the adaptor removed.

FIG. 10A is a side elevation view of pumping assembly 10 showing components of drive 24 mounted within the drive housing 20 while adaptor 38 is mounted to drive housing 20. FIG. 10B is an isometric view of pumping assembly 10 showing removal of bearing plate 46 through adaptor 38. FIG. 10C is a side elevation view of pumping assembly 10 showing components of drive 24 mounted within drive housing 20 with adaptor 38 removed. FIGS. 10A-10C will be discussed together.

The ends of plate body 84 are aligned with voids 116 formed in inner ring 112 of adaptor 38. Projections 118 in inner ring 112 support the material surrounding inner holes 120, facilitating mounting of adaptor 38 to drive housing 20. Voids 116 facilitate installation and removal of bearing plates 46 within drive housing 20 while adaptor 38 remains mounted to drive housing 20. The ends of plate body 84 are aligned with voids 116 such that bearing plate 46 can be removed from drive housing 20 through voids 116 and central aperture 44. Bearing plate 46 can thereby be removed from drive housing 20 while adaptor 38 remains installed on drive housing 20.

As shown, the inner diameter of projections 118 generally would not allow (would block) the bearing plate 46 from being moved past inner ring 112 and out of drive housing 20. The alignment of the ends of plate body 84 with voids 116 between projections 118 allows bearing plate 46 to be removed through adaptor 38 while adaptor 38 remains attached to drive housing 20.

As seen in FIG. 10B, bearing plate 46 has been moved axially outward from drive housing 20 past projections 118 while adaptor 38 remains mounted to drive housing 20. The same or a different bearing plate 46 can be inserted into drive housing 20 through central aperture 44 and past projections 118. Adaptor 38 allows for servicing of drive 24, or for the exchange of different bearing plate 46 types (e.g. fully mechanical or partially mechanical and partially pneumatic/hydraulic as previously described) without removal of the adaptors 38. Adaptor 38 allows for access to and servicing of various components of drive 24. For example, components of motor 12' (FIG. 3B) and its associated drive 24 are disposed fully within drive housing 20. Such components can be accessed and serviced through adaptor 38 while adaptor 38 remains mounted. In some examples, a ball or roller screw forming such a drive 24 can be accessed through central aperture 44 and serviced. For example, such components can be lubricated through central aperture 44.

Accessing drive 24 through central aperture 44 allows the connection between adaptor 38 and drive housing 20 to be maintained during servicing and/or replacement of components of drive 24. Maintaining the connection between adaptor 38 and drive housing 20 while accessing components of drive 24 ensures that the annular seal (e.g., rubber O-ring) disposed at first interface 78 between inner mounting portion 40 and drive housing 20 is maintained. Maintaining first interface 78 ensures sealing of drive chamber 52 (e.g., of the pneumatic or hydraulic charge within the drive chamber 52) and it may be convenient to leave the annular seal in place during servicing, such that it is convenient to remove the bearing plates 46 for servicing and/or changing of configuration without removal of the adaptors 38.

The drive housing 20 includes an extension that is shown orientated horizontally in FIGS. 10-10C. For example, the extension can be a control housing for housing control components of an internally mounted motor or can be the motor and drive train for an externally mounted motor. In some cases, a user might want to change the orientation of the extension to orientate the extension in a more convenient way, such as to minimize the footprint of pump assembly 10 in a crowded facility. For example, the user may desire to orientate the extension vertically instead of horizontally. Either orientation is possible, but inlet check valves 26 and outlet check valves 28 are required to be orientated vertically because the check valves rely at least partially on gravity to transition to a closed state because springs are not used in this embodiment.

Housing holes 130 are evenly arrayed about end 32 of drive housing 20. Housing holes 130 and inner holes 120 being evenly arrayed about pump axis P-P allows drive housing 20 to be oriented in any desired clocked orientation relative to gravity (eight orientations are possible in the example shown) while maintaining the check valves in the required vertical orientation. Due to the asymmetric pattern of outer holes 124 in the adaptor 38, the adaptor 38 must be removed when the orientation of the drive housing 20 is changed.

The different spacing the first subset 126 of outer holes 124 and the second subset 128 of outer holes 124 ensures proper orientation of the inlet check valves 26 and outlet check valves 28 when pump 14 is assembled. The orientation of inlet check valves 26 and outlet check valves 28 follow the orientation of fluid covers 34. As shown in FIG. 10A, indicator 122 is a gap formed between second subset 128 of outer holes 124. In such an example, indicator 122 and second subset 128 of outer holes 124 are intended to always be closest to the ground (relative to the direction of gravity), whereas first subset 126 of outer holes 124 is disposed furthest from the ground (relative to the direction of gravity). The relative position of indictor 122 and thus of first subset 126 and second subset 128 indicate proper orientation of adaptor 38 to ensure that fluid cover 34 is properly orientated. It is understood, however, that indicator 122 can be formed at any desired position on adaptor 38 to indicate the proper orientation of adaptor 38 relative to gravity. For example, indicator 122 can be disposed between first subset 126 of outer holes 124 such that indicator 122 is intended to always be furthest from the ground (relative to the direction of gravity), among other options.

Adaptors 38 including inner holes 120 having consistent spacing so that the adaptor 38 can be mounted to drive housing 20 in any clocked orientation. Adaptors 38 include outer holes 124 having inconsistent spacing so that fluid cover 34 can be mounted to adaptor 38 only in an orientation which properly orientates the inlet check valves 26 and outlet check valves 28. It is expected that adaptor 38 will largely remain in place on drive housing 20 for an extended period (such as initial install by a technician likely to know how to orientate the adaptor 38 for proper fluid cover 34 alignment) while fluid cover 34 will be removed on a more frequent basis to access and service drive 24. Any misalignment between fluid cover 34 and adaptor 38 when fluid cover 34 is reinstalled will be quickly discovered by the technician performing maintenance if adaptor 38 remains in place on drive housing 20 while fluid cover 34 is removed to perform the maintenance. Cover holes 132 (best seen in FIGS. 12A-13A) and outer holes 124 will be misaligned if fluid cover 34 is attempted to be installed in an incorrect orientation. Such misalignment prevents the insertion of fasteners 50*b* through cover holes 132 and outer holes 124 so fluid cover 34 cannot be mounted in an incorrect orientation relative adaptor 38. So long as adaptor 38 remains attached during maintenance, then fluid cover 34 can only be properly connected to adaptor 38 in one orientation, which is the proper orientation.

Figure 11:
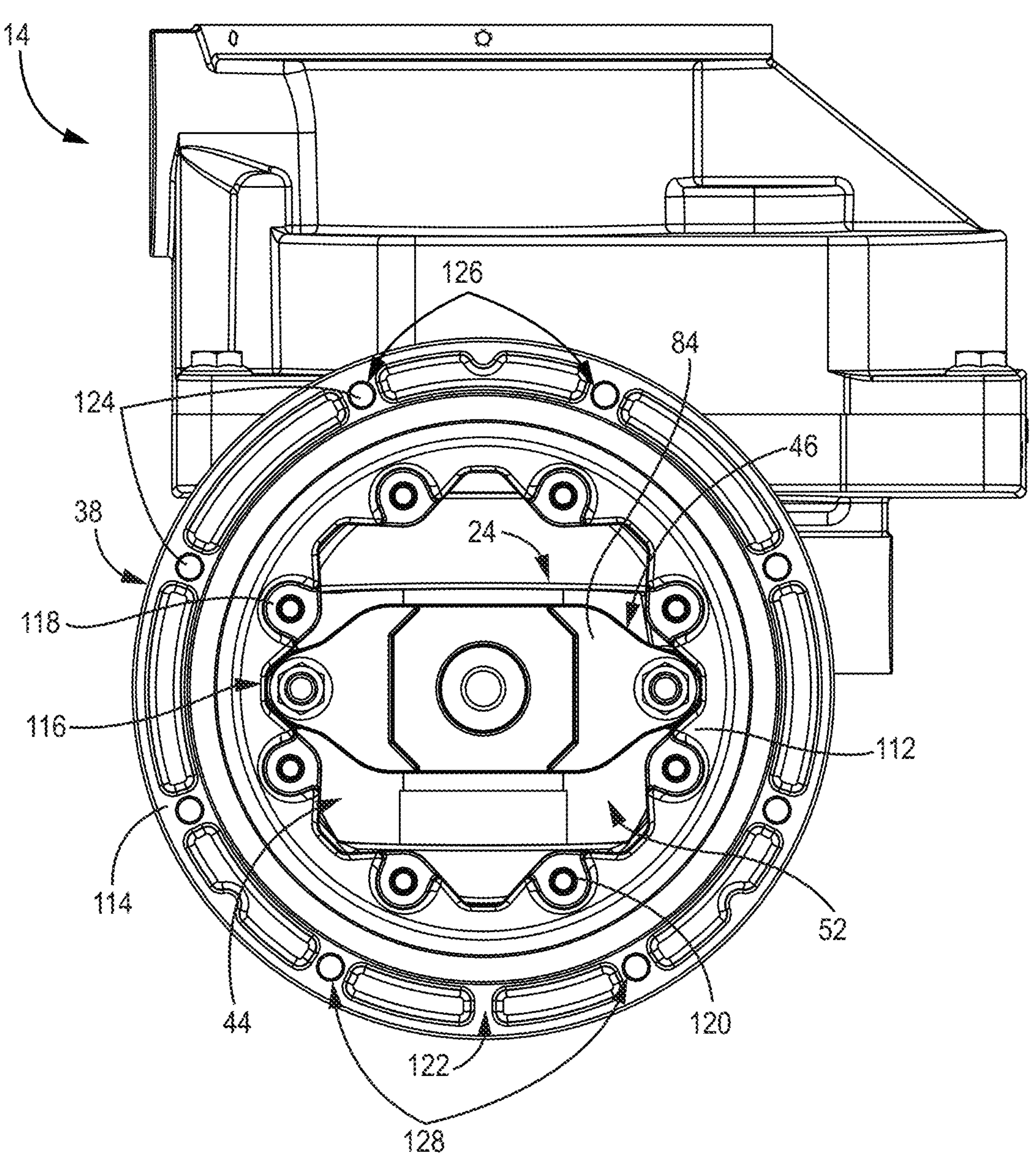
FIG. 11 is a side elevation view of an electrically operated pumping assembly in a vertical orientation with the fluid cover and diaphragm removed.

FIG. 11 is an elevation view of pumping assembly 10 showing pumping assembly 10 in a vertical orientation. FIG. 11 is substantially similar to FIG. 10A except drive housing 20 has been rotated 90-degrees counterclockwise such that the extension from drive housing 20 extends vertically above drive housing 20. As discussed above, the even spacing between inner holes 120 facilitates mounting of adaptor 38 to drive housing 20 in any clocked orientation such that the extension from drive housing 20 extends in any desired direction. Adaptor 38 is mounted to drive housing 20 such that fluid cover 34 must be oriented vertically to ensure proper function of inlet check valves 26 and outlet check valves 28. Indicator 122 is disposed at the bottom of pump assembly 10 and closest to ground relative the direction of gravity, ensuring that fluid cover 34, and thus inlet check valves 26 and outlet check valves 28, are in the proper orientation when pump 14 is fully assembled.

Figures 12A, 12B:
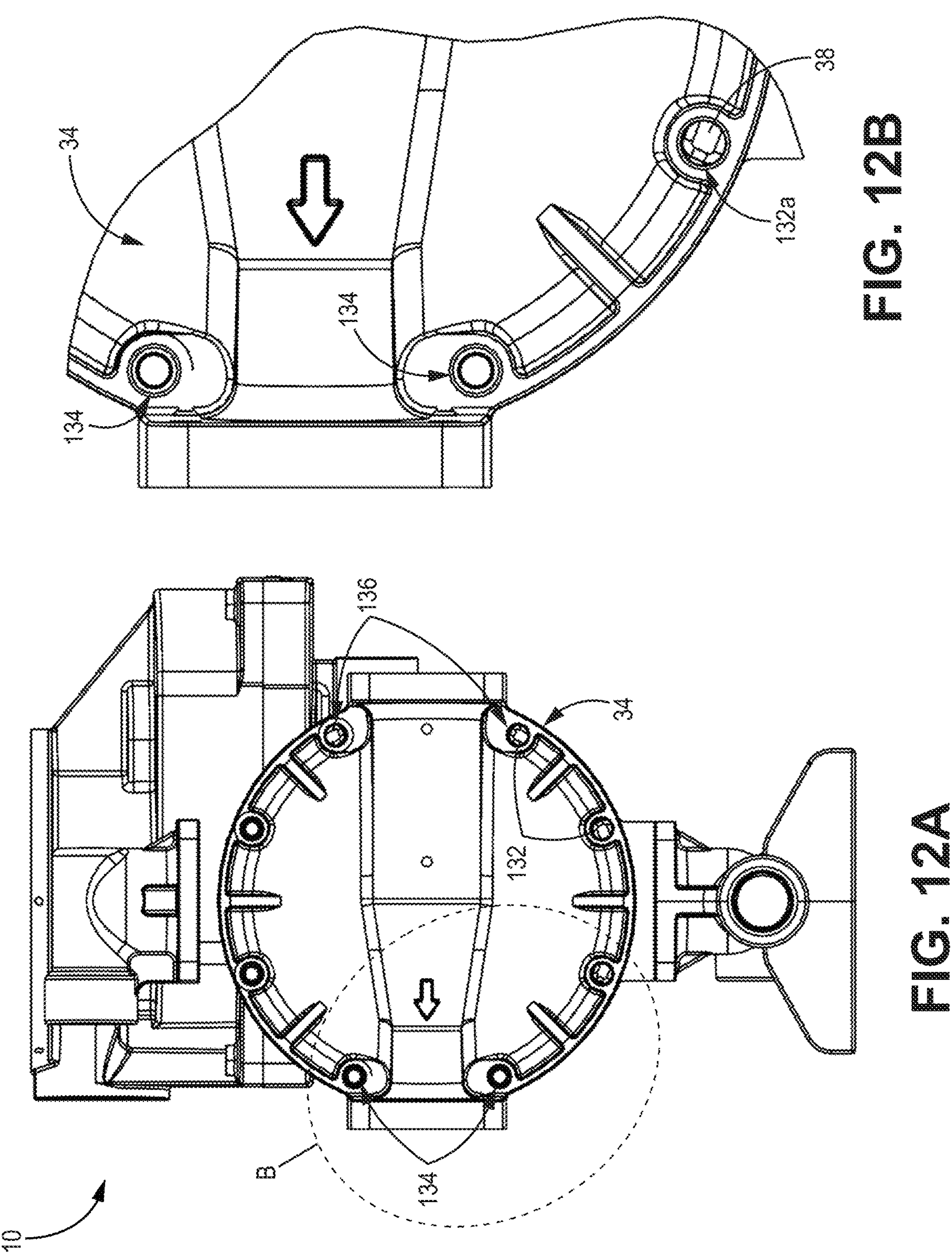
FIG. 12A is a side elevation view of an electrically operated pumping assembly showing a fluid cover in a misaligned position.
FIG. 12B is an enlarged view of detail B in FIG. 12A.

FIG. 12A is an isometric view of pumping assembly 10 showing fluid cover 34 misaligned with adaptor 38 (best seen in FIGS. 9A-9C). FIG. 12B is an enlarged view of detail B in FIG. 12A. Fluid cover 34 includes cover holes 132 that align with outer holes 124 when fluid cover 34 is properly oriented relative to adaptor 38. Cover holes 132 include third subset 134 and fourth subset 136.

Third subset 134 of cover holes 132 have a first spacing therebetween and fourth subset 136 of cover holes 132 have a second spacing therebetween. The first spacing is different from the second spacing. The difference in the spacing provides mistake-proofing that ensures fluid cover 34 is properly aligned with adaptor 38. The uneven spacing between cover holes 132 prevents fluid cover 34 from being mounted to adaptor 38 in an incorrect orientation.

The spacing between third subset 134 of cover holes 132 and first subset 126 of outer holes 124 is the same. The spacing between fourth subset 136 of cover holes 132 and second subset 128 of outer holes 124 is the same. Such spacing ensures that third subset 134 of cover holes 132 interface with first subset 126 of outer holes 124 and that fourth subset 136 of cover holes 132 interface with second subset 128 of outer holes 124 when fluid cover 34 is mounted. Fluid cover 34 cannot be mounted to adaptor 38 except by aligning third subset 134 of cover holes 132 with first subset 126 of outer holes 124 and fourth subset 136 of cover holes 132 with second subset 128 of outer holes 124.

Fluid cover 34 is shown as misaligned in FIGS. 12A and 12B. Fluid cover 34 is shown in the orientation corresponding to the motor extension extending horizontally (as shown in FIGS. 10A-10C). As best seen in FIG. 12B, the difference in hole pattern spacing results in a mismatch at hole 132*a* of fluid cover 34 such that there is no corresponding outer hole 124 aligned with hole 132*a*. The pathway through hole 132*a* is thereby blocked preventing the insertion of a fastener 50*b* through fluid cover 34 and adaptor 38 at that location. A portion of adaptor 38 is visible through hole 132*a*, which portion prevents the insertion of the fastener 50*b* through hole 132*a*. Fluid cover 34 cannot be fixed to adaptor 38 due to the misalignment. The inability to insert a fastener 50*b* provides a signal to the technician that fluid cover 34 is misaligned on adaptor 38. Inlet manifold 16 and outlet manifold 18 are shown in their proper positions in FIG. 12A, but it is understood that inlet manifold 16 and outlet manifold 18 are typically installed after fluid covers 34, such that their positioning does not indicate the proper orientation of fluid cover 34 to the user.

Figure 13A:
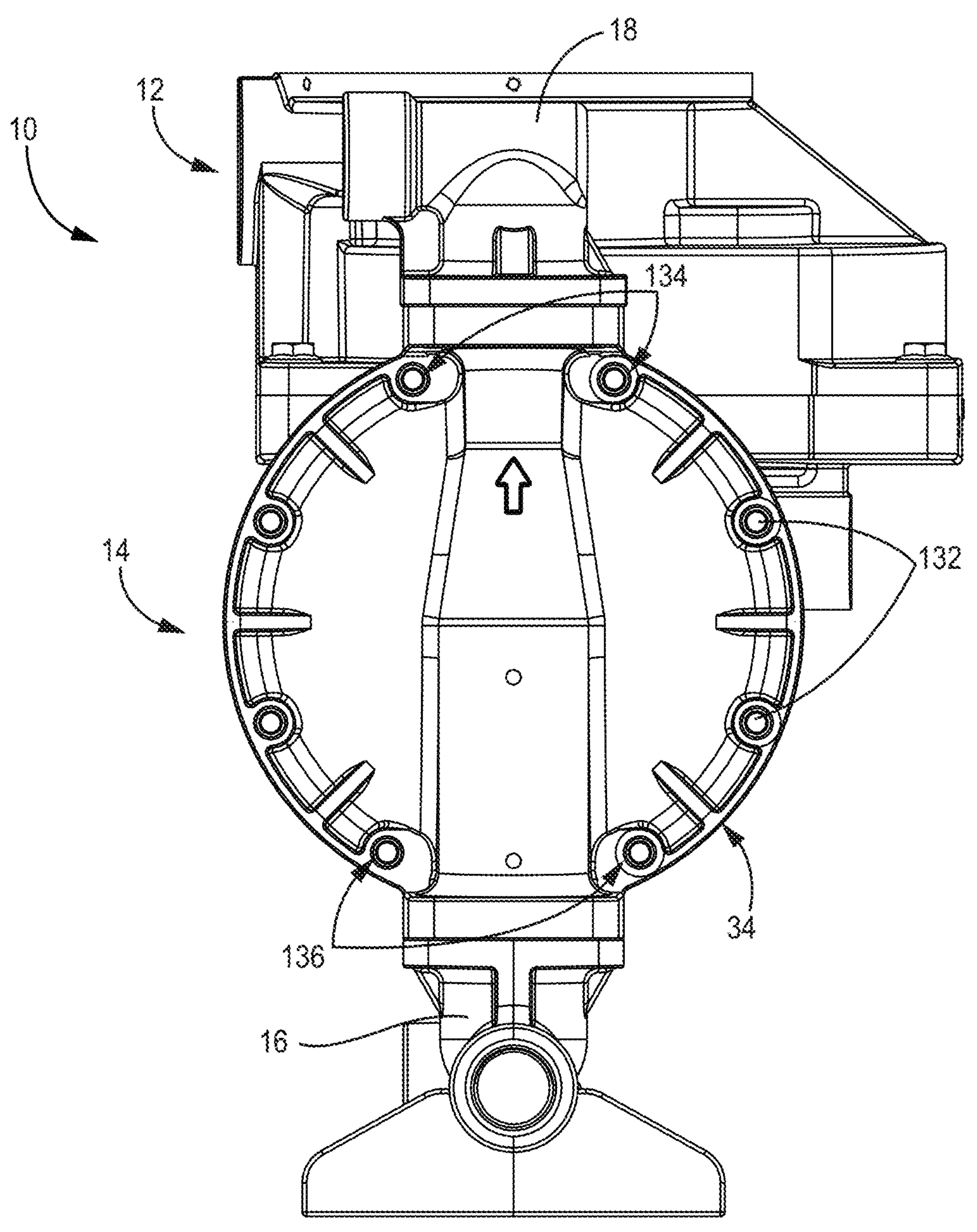
FIG. 13A is a side elevation view of an electrically operated pumping assembly showing a fluid cover correctly aligned.
Figure 13B:
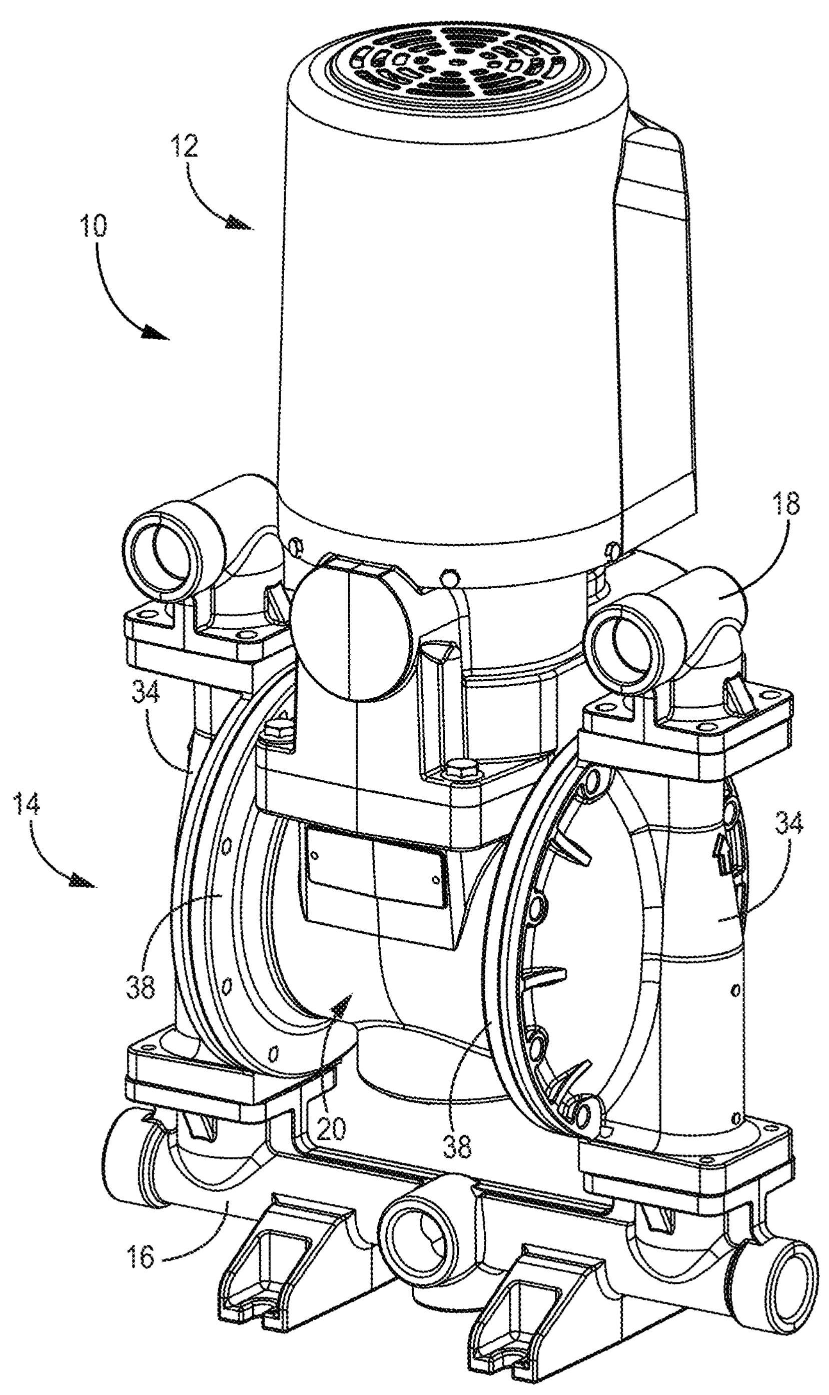
FIG. 13B is an isometric view showing the electrically operated pumping assembly assembled in a vertical state.

FIG. 13A is a side elevation view of pumping assembly 10 showing fluid cover 34 properly aligned on pumping assembly 10 and mounted to adaptor 38. FIG. 13B is an isometric view of pumping assembly 10 with motor 12 oriented vertically. Fluid cover 34 is shown as correctly oriented such that all cover holes 132 are aligned with an outer hole 124 through adaptor 38. Fasteners 50*b* can thereby be inserted through cover holes 132 and into outer holes 124 to fix fluid cover 34 to adaptor 38. Inlet manifold 16 and outlet manifold 18 are mounted to fluid cover 34 and inlet check valves 26 and outlet check valves 28 are in the proper orientation relative gravity.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A displacement pump system comprising:
- a drive housing defining a pump axis;
- a first fluid module mountable to an end of the drive housing, the first fluid module including:
  - a first adaptor configured to interface with the drive housing, the first adaptor comprising a first inner mounting portion and a first outer mounting portion, wherein the first inner mounting portion interfaces with the drive housing at a first interface;
  - a first cover configured to interface with the first outer mounting portion at a second interface; and
  - a first diaphragm captured between the first adaptor and the first cover;
- a second fluid module mountable to the end of the drive housing in place of the first fluid module, the second fluid module including a second adaptor configured to interface with the drive housing, a second cover that mounts to the second adaptor, and a second diaphragm captured between the second adaptor and the second cover;
- wherein the first diaphragm is a different size than the second diaphragm.

2. The system of claim 1, wherein the first inner mounting portion includes a plurality of inner openings configured to receive fasteners to mount the first adaptor to the drive housing.

3. The system of claim 2, wherein the drive housing includes a plurality of housing openings configured to receive the fasteners extending through the inner openings.

4. The system of claim 3, wherein the plurality of inner openings and the plurality of housing openings are arranged such that each one of the plurality of inner openings is aligned with one of the plurality of housing openings with any one of the plurality of inner openings aligned with a first one of the plurality of housing openings.

5. The system of claim 2, wherein the plurality of inner openings are evenly arrayed around the first inner mounting portion.

6. The system of claim 5, wherein the plurality of inner openings are formed on a radial portion of the first inner mounting portion that extends radially inward from a transition portion to the first adaptor.

7. The system of claim 2, wherein voids are disposed between adjacent ones of the plurality of inner openings.

8. The system of claim 7, wherein a first ring defined by apexes of the voids has a first diameter, a second ring defined by the fastener openings has a second diameter, and the first diameter is larger than the second diameter.

9. The system of claim 1, wherein a drive component is disposed within the drive housing and connected to the first diaphragm, and wherein the drive component is configured to receive driving power from an electric motor and to output the driving power to the first diaphragm to drive the first diaphragm through a suction stroke.

10. The system of claim 9, wherein the drive component is further configured to drive the first diaphragm through a pressure stroke, and wherein the drive component is removable from the drive housing through the first adaptor.

11. The system of claim 9, wherein the drive component is configured to provide a linear input to the first diaphragm based on a rotational output from the motor of the electric drive.

12. The system of claim 11, wherein the drive component is disposed coaxially with the motor.

13. The system of claim 1, wherein the first outer mounting portion includes a plurality of outer openings configured to receive fasteners to mount the first cover to the first adaptor.

14. The system of claim 1, wherein:

the first interface allows the first adaptor to be mounted at a plurality of adaptor mount positions; and the second interface is a clocked interface that allows the first cover to be mounted at a single cover mount position and prevents the first cover from being mounted at orientations other than the single cover mount position.

15. The system of claim 1, wherein:

the first outer mounting portion includes a plurality of outer openings configured to receive fasteners to mount the first cover to the first adaptor; and the plurality of outer openings are unevenly arrayed about the first outer mounting portion.

16. The system of claim 1, wherein the first adaptor has a first inner diameter and a first outer diameter, wherein the second adaptor has a second inner diameter and a second outer diameter, and wherein the first outer diameter differs from the second outer diameter.

17. The system of claim 16, wherein the first inner diameter is the same as the second inner diameter.

18. A displacement pump system comprising:

an electric drive having a drive housing defining a pump axis;

a first fluid module mountable to an end of the drive housing, the first fluid module including:

a first adaptor configured to interface with the drive housing, the first adaptor comprising a first inner mounting portion and a first outer mounting portion, the first inner mounting portion configured to interface with the drive housing at a first interface;

a first cover configured to interface with the first outer mounting portion at a second interface; and a first diaphragm captured between the first adaptor and the first cover;

a second fluid module mountable to the end of the drive housing in place of the first fluid module, the second fluid module including a second adaptor configured to interface with the drive housing at the first interface in place of the first adaptor, a second cover that mounts to the second adaptor, and a second diaphragm captured between the second adaptor and the second cover;

wherein the second adaptor includes a second inner mounting portion and a second outer mounting portion, the second inner mounting portion configured to interface with the drive housing at the first interface;

wherein a first diameter of the first diaphragm is different than a second diameter of the second diaphragm.

19. The system of claim 18, wherein:

the first interface allows either one of the first adaptor and the second adaptor to be mounted at a plurality of adaptor mount positions.

20. The system of claim 18, wherein:

the first inner mounting portion includes a plurality of first inner openings configured to receive first fasteners to mount the first adaptor to the drive housing; and the second inner mounting portion includes a plurality of second inner openings configured to receive the first fasteners to mount the second adaptor to the drive housing.

* * * * *